United States Patent [19]
Yoshida et al.

[11] Patent Number: 5,985,177
[45] Date of Patent: Nov. 16, 1999

[54] O/W/O TYPE MULTIPLE EMULSION AND METHOD OF PREPARING THE SAME

[75] Inventors: Katsunori Yoshida; Toshio Yanaki; Michihiro Yamaguchi; Hiroko Watanabe; Takafumi Kurosawa; Kenzo Ito, all of Yokohama, Japan

[73] Assignee: Shiseido Co., Ltd., Tokyo, Japan

[21] Appl. No.: 08/739,146

[22] Filed: Oct. 28, 1996

[30] Foreign Application Priority Data

| | | | |
|---|---|---|---|
| Dec. 14, 1995 | [JP] | Japan | 7-347770 |
| Jan. 26, 1996 | [JP] | Japan | 8-32949 |
| Feb. 13, 1996 | [JP] | Japan | 8-50833 |
| Mar. 28, 1996 | [JP] | Japan | 8-99244 |
| Jun. 14, 1996 | [JP] | Japan | 8-175711 |
| Jul. 15, 1996 | [JP] | Japan | 8-205428 |

[51] Int. Cl.⁶ .............................. A61K 7/44; B01J 13/00
[52] U.S. Cl. ......................... 252/309; 252/314; 424/60; 424/401; 514/725
[58] Field of Search .................... 252/309, 314; 424/60, 401

[56] References Cited

U.S. PATENT DOCUMENTS

| | | | |
|---|---|---|---|
| 3,395,028 | 7/1968 | Mackles | 106/8 |
| 4,013,475 | 3/1977 | Liebowitz et al. | 252/309 X |
| 5,391,321 | 2/1995 | Grüning et al. | 252/309 |
| 5,429,999 | 7/1995 | Haé et al. | 252/315.2 X |

FOREIGN PATENT DOCUMENTS

| | | |
|---|---|---|
| 0 048 153 | of 0000 | European Pat. Off. . |
| 0 331 833 | 9/1989 | European Pat. Off. . |
| 0 614 660 | 9/1994 | France . |
| 55-33294 | 3/1974 | Japan . |
| 57-29213 | 6/1982 | Japan . |
| 33-54709 | 11/1984 | Japan . |
| 2-32015 | 9/1986 | Japan . |
| 63 030405 | 2/1988 | Japan . |
| 63-30405 | 2/1988 | Japan . |
| 7-101844 | 4/1995 | Japan . |
| 08 323188 | 12/1996 | Japan . |

OTHER PUBLICATIONS

Journal of the Japan Oil Chemists' Society, vol. 40, No. 6, pp. 491–496 (1991).
Patent Abstracts of Japan, JP 61 129033A, Shiseido Co., Ltd., Jun. 17, 1986, Japan.
Patent Abstracts of Japan, JP 62 030547, Feb. 9, 1987, Japan.

*Primary Examiner*—Richard D. Lovering
*Attorney, Agent, or Firm*—Ronald R. Snider

[57] ABSTRACT

This invention relates to an oil-in-water-in-oil (O/W/O) type multiple emulsion which contains an inner oil phase, a water phase, and an outer oil phase. The inner oil phase is first dispersed in water to form an oil-in-water (O/W) emulsion. Then, the O/W emulsion is further dispersed in the outer oil phase to form the O/W/O type multiple emulsion. The outer oil phase contains an organophilic clay mineral, which can effectively prevent the inter-mixing of the inner oil phase with the outer oil phase, thus, producing an O/W/O type multiple emulsion with excellent storage stability. Upon the using of an oil-soluble compound in the inner oil phase, this multiple emulsion system can prevent the oil-soluble compound from being oxidized. In addition, since different kinds of oils can be selected for the making of the inner and outer oil phases, respectively, the O/W/O type multiple emulsion system allows one to present two different kinds of oils, which have different properties independent from each other, in one emulsion system.

19 Claims, 1 Drawing Sheet

O/W/O TYPE MULTIPLE EMULSION AND METHOD OF PREPARING THE SAME

RELATED APPLICATIONS

This application claims the priority of Japanese Patent Application No. 7-347770 filed on Dec. 14, 1995, 8-32949 filed on Jan. 26, 1996, 8-50833 filed on Feb. 13, 1996, 8-99244 filed on Mar. 28, 1996, 8-175711 filed on Jun. 14, 1996, and 8-205428 filed on Jul. 15, 1996 which are incorporated herein by reference.

FIELD OF THE INVENTION

The present invention relates to an O/W/O type multiple emulsion and a method of making the same and, in particular, to prevention of its inner oil phase and outer oil phase from combining together and further to improvement in stabilization of oil-soluble agents blended in the inner oil phase.

BACKGROUND OF THE INVENTION

Oil-in-water-in-oil type (referred to as "O/W/O type" in the following) emulsion composition in which an oil-in-water type (referred to as "O/W type" in the following) emulsion is further emulsified and dispersed in an oil phase, also known as complex emulsion or multiple emulsion, have become important in various industrial uses such as cosmetics, food products, and medicines. Namely, while normal W/O type emulsions have a configuration in which a water phase is simply dispersed in an oil phase, the particle structure of multiple emulsions is such that, as shown in FIG. 1, an inner oil phase 14 is further dispersed in a water phase 12 which has been dispersed in an outer oil phase 10. Accordingly, they are expected to yield special feel of use and effects which cannot be obtained by simple O/W type and W/O type emulsions.

For example, since the inner oil phase 14 is blocked from the external atmosphere by the water phase 12 and the outer oil phase 10, when an oil-soluble material which is easily oxidized is contained in the inner oil phase 14, its stability against oxidization is expected to be improved as compared with the cases where it is contained in the oil phase of O/W type or W/O type emulsions.

Also, in recent years, silicone type bases such as dimethylpolysiloxane have been widely used as a base for external preparations for skin or cosmetic preparations due to their favorable usabilities such as good spreadability, refreshness, and lack of greasiness, as well as their excellent water resistance and oil resistance which make them resistant to being washed out by sweat and water. In particular, in suncare cosmetics, since they are universally used in summer, refreshing feel of use and those not easily washed out by sweat, sebum, or water are required, whereby such silicone bases are being used more frequently.

Of the oil-soluble agents usually added in cosmetic preparations and external preparations for skin, those hard to dissolve in silicone type oils are not a few, however. For example, of the oil-soluble ultraviolet absorbers added in suncare cosmetic preparations, there are many which have a remarkably low solubility to silicone type bases. Accordingly, in cosmetic preparations containing a large amount of a silicone type base, there has been a problem that, when such an ultraviolet absorber is added therein, crystals of the ultraviolet absorber may deposit over time.

In order to prevent crystals from depositing, it has been necessary to restrict the using amount of oil-soluble agents which are hard to dissolve in silicone type oils or concurrently use a large amount of oils such as polar oils to which the agents have a high solubility. Effect of the agent, however, usually depend on its amount added and cannot be sufficiently obtained when the using amount is restricted. Also, when non-silicone type oils such as polar oils are used in a large amount, the amount of silicone type oils is restricted in emulsion compositions, for example, due to problems in terms of formulation, whereby there are cases in which a large amount of silicone type oils cannot be added to make it difficult to yield satisfactory feel of use and resistance to both water and oil.

Further, since silicone type oils are totally different from the other polar and nonpolar oils in terms of structure and property, when non-silicone type oils added in an oil phase of an emulsion such as W/O or O/W together with a silicone type oil, it is difficult to select an emulsifier, emulsification conditions, and the like, thereby making it quite difficult, in general, to obtain an emulsion having a favorable emulsion stability.

These problems are considered to be solved by application of O/W/O type multiple emulsion. Namely, in an O/W/O type multiple emulsion, since an inner oil phase 14 and an outer oil phase 10 are separated from each other by a water phase 12, it is theoretically possible to make two kinds of oil contents such as a silicone type oil and a non-silicone type oil which have different properties coexist independently from each other in one emulsion system. For example, when an oil-soluble material which is hard to dissolve in a silicone type oil and a non-silicone type oil to which the material is soluble are added in one oil phase, whereas the silicone type oil is added in the other oil phase, the material can be prevented from depositing while these components are made to coexist stably in one emulsion system.

As a method of preparing a multiple emulsion, there has conventionally been known a so-called two-step emulsion technique in which an O/W type emulsion formed by using a hydrophilic surfactant 16 is re-emulsified in an outer oil phase in which a lipophilic surfactant 18 has been dissolved. However, the emulsification stability of thus prepared multiple emulsion may be so low that, over time, the inner oil phase 14 and the outer oil phase 10 can merge with each other or the water phase 12 can be incorporated therein, thereby finally dissociating the oils or water. Since the emulsification stability of the multiple emulsion itself is quite low, the above-mentioned effects expected from the O/W/O type multiple emulsion have not been fully attained.

In order to overcome these problems, various attempts have been made. For example, Japanese Examined Patent Publication No. 55-33294 discloses a method in which a milk protein and cane sugar fatty acid ester are used together, while Japanese Examined Patent Publication No. 3-54709 discloses a method in which polyglycerine fatty acid ester is compounded in the outer oil phase. Also, Japanese Unexamined Patent Publication No. 63-30405 discloses a method in which a specific kind of bentonite and dextrin fatty acid ester are respectively compounded in the water phase and the outer oil phase.

However, even in the O/W/O type multiple emulsions prepared by the above-mentioned conventional methods, the inner oil phase still tends to merge with the outer oil phase, thereby reducing the remaining amount of the inner oil phase over time. Namely, since the inner oil phase 14 and the outer oil phase 10 face each other with the water phase 12 and hydrophilic groups of the surfactants 16 and 18 therebetween, there is only a very small barrier for preventing these oil phases 10 and 14 from merging with each other. Also, since the inner oil phase 14 has to be present, it is difficult, physically or in techniques of manufacture, for the water phase 12 to have a small particle size. Accordingly, the O/W/O type multiple emulsion has a greater number of causes for unstableness as compared with the conventional O/W type or W/O type emulsions. Therefore, the products prepared by the above-mentioned methods have a shortcomings that the characteristics of the multiple emulsion are not sufficiently represented in their physical properties.

Also, while an O/W/O type multiple emulsion in which an ultraviolet absorber or an antioxidant is compounded in its inner oil phase has recently been reported in Japanese Unexamined Patent Publication No. 7-101844, since the conventional technique is used for preparing such a multiple emulsion, its emulsification stability tends to be so low that the emulsion condition may be collapsed during a long period of storage, whereby the stability of the agent compounded in the inner oil phase against oxidization over time can not be improved.

Thus, in the conventional multiple emulsions, those which are stable over time cannot be easily obtained. Also, for example, even when an oil-soluble agent is contained in the inner oil phase at the time of preparation, the inner oil phase may merge with the outer oil phase over time, thereby reducing the remaining amount of the inner oil phase and finally incorporating the inner oil phase into the outer oil phase. Accordingly, the agent and the oil in the inner oil phase may migrate to the outer oil phase, whereby the effects expected from the O/W/O type emulsion composition cannot be sufficiently obtained.

Also, in order to improve the stability of an emulsion, the above-mentioned conventional methods include a step for rapidly cooling and plasticizing the emulsion subsequent to the heating step during its preparation. In this case, the heating and rapid cooling steps necessitate a special apparatus and, accordingly, it is quite difficult for thermally unstable ingredients such as vitamins to be compounded.

SUMMARY OF THE INVENTION

In view of the foregoing problems of the prior art, the object of the present invention is to provide a multiple emulsion having stabilities of the emulsified condition and the agent over time due to preventing its inner oil phase and outer oil phase from combining together.

As a result of diligent studies to achieve the above-mentioned object, the inventors have found that the inner oil phase and outer oil phase are remarkably prevented from combining together when an organophilic clay mineral is present in the outer oil phase. It has also been found that, when an oil-soluble material is contained in the inner oil phase in such a multiple emulsion system, the material is prevented from being oxidized and decomposed during a long period without migrating to the outer oil phase. Thus, the present invention has been accomplished.

Namely, the multiple emulsion in accordance with the present invention is an O/W/O type multiple emulsion in which an O/W type emulsion is dispersed in a continuous outer oil phase, wherein said outer oil phase contains an organophilic clay mineral.

Preferably, the organophilic clay mineral is obtained from a water-swellable clay mineral by treating with a quaternary ammonium type cationic surfactant and a nonionic surfactant.

Preferably, a blending ratio of the oil-in-water type emulsion to the outer oil phase is within a range of 2:3 to 19:1 by weight ratio.

Preferably, in the multiple emulsion in accordance with the present invention, the silicone type oil is contained in the oil phase.

Preferably, the silicone type oil is contained in the outer oil phase.

Preferably, the silicone type oil is within a range of 5 to 60 weight % with respect to a whole amount of the multiple emulsion.

Preferably, the silicone type oil has a boiling point which is 200° C. or less.

Preferably, in the multiple emulsion in accordance with the present invention, an inner oil phase contains an oil-soluble material.

Preferably, the oil-soluble material contained in the inner oil phase is slightly soluble in a silicone type oil and the silicone type oil is blended in the outer oil phase.

Also, the oil-soluble material included in the inner oil phase is preferably one or more agent selected from the group consisting of oil-soluble vitamins, oil-soluble ultraviolet absorbers, and unsaturated fatty acids and the derivatives thereof which are easily oxidized.

Preferably, in the multiple emulsion in accordance with the present invention, a water phase contains a hydrophilic polymer.

Preferably, the hydrophilic polymer is one or more selected from the group of sodium alginate, carageenan, xanthan gum, gelatin, curdlan, agar, glucomannan, starch, hyaluronic acid, scleroglucan, schizophyllan, lentinan, pararomine, callose, raminarun, cellulose, methylcellulose, ethylcellulose, nitrocellulose, gum arabic, polyvinyl alcohol, carboxyvinyl polymer, carboxymethylcellulose, hydroxyethylcellulose, polyethylene glycol, tragacanth gum, garactan, guar gum, carob gum, karaya gum, pectin, guince seed, argecolloids, glycyrrhizinic acid, dextran, puluran, collagen, casein, albumen, carboxymethyl starch, methylhydroxypropyl starch, methylhydroxypropylcellulose, sodium cellulose sulfate, hydroxypropylcellulose, propylene glycol alginate, polyvinylmethyl ether, polyvinyl pyrrolidone, polyoxyethylene polyoxypropylene copolymer, sodium polyacrylate, polyethylacrylate, polyacryl amide, and polyethylene imine.

The method of preparing an oil-in-water-in-oil type multiple emulsion in accordance with the present invention comprises the steps of:

preparing an oil in water-soluble solvent type emulsion by blending components of an inner oil phase into a mixture of a hydrophilic nonionic surfactant and a water-soluble solvent;

preparing an oil-in-water type emulsion by blending components of a water phase into said oil in water-soluble solvent type emulsion; and preparing an oil-in-water-in-oil type multiple emulsion by dispersing and emulsifying said oil-in-water type emulsion in a mixture of components of an outer oil phase which contains an organophilic clay mineral.

Preferably, in the method of the present invention, a silicone type oil is contained in the oil phase.

Preferably, in the method of the present invention, the silicone type oil is contained in the outer oil phase.

Preferably, in the method of the present invention, the inner oil phase contains an oil-soluble material.

Preferably, in the method of the present invention, the oil-soluble material contained in the inner oil phase is slightly soluble in a silicone type oil and the silicone type oil is contained in the outer oil phase.

Preferably, in the method of the present invention, the oil-soluble material included in the inner oil phase is one or more agent selected from a group consisting of oil-soluble vitamins, oil-soluble ultraviolet absorbers, and unsaturated fatty acids and the derivatives thereof which are easily oxidized.

Preferably, in the method of the present invention comprises the steps of:

preparing an oil in water-soluble solvent type emulsion by blending components of an inner oil phase into a mixture of a hydrophilic nonionic surfactant and a water-soluble solvent;

preparing an oil-in-water type emulsion by blending components of a water phase which contains water and a hydrophilic polymer into said oil in water-soluble solvent type emulsion;

preparing an oil-in-water-in-oil type multiple emulsion by dispersing and emulsifying said oil-in-water type emulsion in a mixture of components of an outer oil phase which contains an organophilic clay mineral; and making the water phase gel by blending gelling agent of the hydrophilic polymer into said oil-in-water-in-oil type multiple emulsion.

In the following, the configuration of the present invention will be explained in detail.

When a hydrophilic surfactant is used to prepare an O/W type emulsion and then thus prepared emulsion and oil of an outer oil phase containing an organophilic clay mineral are mixed and emulsified together, the O/W/O type multiple emulsion (which may be simply referred to as "multiple emulsion" in the present application) of the present invention is prepared.

As mentioned below, the organophilic clay mineral used in the present invention may be obtained when a water-swellable clay mineral is treated with a quaternary ammonium type cationic surfactant and a nonionic surfactant.

The water-swellable clay mineral used here may be a kind of colloidal hydrous aluminum silicate generally expressed by the following formula I:

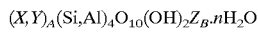
$(X,Y)_A(Si,Al)_4O_{10}(OH)_2Z_B \cdot nH_2O$   formula I wherein

X=Al, Fe$^{III}$, Mn$^{III}$, or Cr$^{III}$;

Y=Mg, Fe$^{II}$, Ni, Zn, or Li;

Z=K, Na, or Ca;

A is 2 to 3; and B=1/3.

Specific examples thereof include natural or synthetic (where OH group in the formula is substituted by fluorine) montmorillonite group such as montmorillonite, saponite, and hectorite as well as synthetic mica known under such names as sodium silicic mica sodium or lithium taeniolite. The montmorillonite group includes commercially available products such as Beegum, Kunipia, and Laponite, and the synthetic mica includes commercially available products such as Dimonite manufactured by Topy Industries, Ltd.

Also, as the quaternary ammonium salt type cationic surfactant, that expressed by the following formula II may be used:

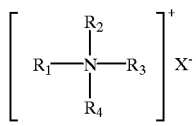

formula II wherein $R_1$ is an alkyl group having 10 to 22 carbon atoms or benzyl group, $R_2$ is methyl group or alkyl group having 10 to 22 carbon atoms, $R_3$ and $R_4$ are alkyl or hydroxyalkyl group having 1 to 3 carbon atoms, and X is halogen atom or methyl sulfate residue.

Examples thereof include dodecyltrimethylammonium chloride, myristyl trimethylammonium chloride, cetyltrimethyl ammonium chloride, stearyltrimethyl ammonium chloride, arachyltrimethyl chloride, behenyltrimethylammonium chloride, myristyldimethylethylammonium chloride, cetyldimethylethylammonium chloride, chloride, arachyldimethylethylammonium chloride, behenyldimethylethylammonium chloride, myristyldiethylmethylammonium chloride, cetyldiethylmethylammonium chloride, stearyldiethylmethylammonium chloride, arachyldiethylmethylammonium chloride, behenyldiethylmethylammonium chloride, benzyldimethylmyristylammonium chloride, benzyldimethylcetylammonium chloride, benzyldimethylstearylammonium chloride, benzyldimethylbehenylammonium chloride, benzylmethylethylcetylammonium chloride, benzylmethylethylstearylammonium chloride, dibehenyldihydroxyethyl ammonium chloride, and their corresponding bromides as well as dipalmitylpropylethyl ammonium methyl sulfate.

In the present invention, at least one of the above-mentioned members may be arbitrarily selected.

Next, the nonionic surfactant used for treating the water-swellable clay mineral together with the above-mentioned quaternary ammonium salt type cationic surfactant will be explained.

The nonionic surfactant used for the treatment of the clay mineral in the present invention has an HLB value preferably within the range of 2 to 16 and more preferably within the range of 3 to 12.

Here, the HLB value is calculated by the following Kawakami's expression:

HLB=7+11.7×log (Mw/Mo)

wherein Mw is molecular weight of the part of the hydrophilic group and Mo is molecular weight of the part of the lipophilic group.

Examples thereof include ethylene oxide addition type surfactants including ether type surfactants such as oleyl ether added with 2 to 30 moles of polyoxyethylene (referred to as POE(2-30) in the following), POE(2-35) stearyl ether, POE(2-20) lauryl ether, POE(1-20) alkyl phenyl ether, POE (6-18) behenyl ether, POE(5-25) 2-decylpentadecyl ether, POE(3-20) 2-decyltetradecyl ether, and POE(8-16) 2-octyldecyl ether; ester type surfactants such as POE(4-60) hardened castor oil, POE(3-14) fatty acid monoester, POE (6-30) fatty acid diester, and sorbitan fatty acid ester; and ether ester type surfactants such as POE(2-30) glyceryl monoisostearate, POE(10-60) glyceryl triisostearate, POE (7-50) castor oil monoisostearate, and POE(12-60) castor oil triisostearate. Also, examples of the nonionic surfactant include polyhydric alcohol fatty acid ester type surfactants including polyglycerine fatty acid esters such as decaglyceryl tetraoleate, hexaglyceryl triisostearate, tetraglyceryl diisostearate, diglyceryl diisostearate and glycerine fatty acid esters such as glyceryl monoisostearate and glyceryl monooleate, and include nonionic modified silicone surfactant such as dimethylpolysiloxane polyoxyalkylene copolymer shown by the following formula III;

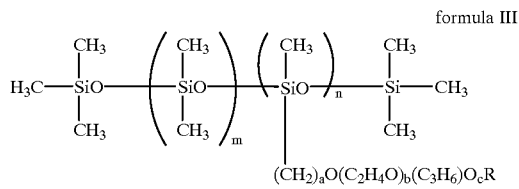

formula III wherein a is an integer from 1 to 5, b is an integer from 7 to 15, c is an integer from 0 to 4, m is an integer from 20 to 100, n is an integer from 1 to 5, and R is hydrogen or an alkyl group having 1 to 5 carbon atoms.

Among these ingredients, in particular, the follows are preferably used; polyglycerine fatty acid esters not lower than triglycerine such as decaglyceryl tetraoleate, hexaglyceryl triisostearate, and tetraglyceryl diisostearate; ethylene oxide addition type nonionic surfactants including POE-added ether type surfactants such as POE(2-12) oleyl ether, POE(3-12) stearyl ether, POE(2-10) lauryl ether, POE(2-10) nonylphenyl ether, POE(6-15) behenyl ether, POE(5-20) 2-decylpentadecyl ether, POE(5-17) 2-decyltetradecyl ether, and POE(8-16) 2-octyldecyl ether; POE-added ester type surfactants such as POE(10-20) hardened castor oil, POE (5-14) monooleate, POE(6-20) dioleate, POE(5-10) sorbitan oleate; and POE-added ether ester type surfactants such as POE(3-15) glyceryl monoisostearate and POE(10-40) glyceryl triisostearate; and nonionic modified silicone surfactant such as dimethylpolysiloxane polyoxyalkylene copolymer shown by formula III mentioned above.

In the present invention, at least one of these nonionic surfactants may be arbitrarily selected for use.

The organophilic clay mineral used in the present invention can be obtained when a water-swellable clay mineral, a quaternary ammonium salt type cationic surfactant, and a nonionic surfactant are dispersed and stirred in a low-boiling solvent such as water, acetone, or lower alcohol and then the low-boiling solvent is removed. Alternatively, it may be obtained when, after the water-swellable clay mineral and the quaternary ammonium salt type cationic surfactant are treated in a low-boiling solvent so as to yield a cationic denatured clay mineral, the latter is treated with the nonionic surfactant and then the low-boiling solvent is removed.

In the following, thus prepared organophilic clay mineral will be explained. Among clay minerals, Na-type montmorillonite, for example, which belongs to smectites and is water-swellable, becomes a hydrophobic organophilic montmorillonite upon cation exchange reaction with a quaternary ammonium salt type organic cation. Further, it encloses the nonionic surfactant so as to form an inclusion compound which may be referred to as "complex", and then swells in an oil to form a viscous oily gel. It is considered that the nonionic surfactant is enclosed in a polar site between montmorillonite layers (which may be referred to as "silicate layers") which does not participate in the cation exchange reaction and that the oil further infiltrates between these layers such that the layers swell and form an oily gel (Journal of the Japan Oil Chemists' Society, vol. 40, no. 6, pp. 491–496, 1991).

Thus obtained organophilic clay mineral has such a structure that the distance between the layers of the water-swellable clay mineral is broadened due to the quaternary ammonium type cationic surfactant and nonionic surfactant infiltrating therein. Accordingly, when the long surface distance is measured by X-ray diffraction, it can be confirmed whether the quaternary ammonium type cationic surfactant and the nonionic surfactant are chemically and physically adsorbed or not.

Also, when thus obtained organophilic clay mineral is subjected to Soxhlet extraction by using chloroform, ether, or the like, the surfactant physically adsorbed between the layers is washed out. Accordingly, when this extract is subjected to gas chromatography analysis, measurement of the thermal decomposition temperature, or measurement of the thermal decomposition amount (DTA-TG measurement), the amount of the surfactant physically adsorbed can be confirmed. Here, since the amount of the quaternary ammonium salt type cationic surfactant which is chemically bonded in organophilic clay mineral due to cationic exchange cannot be extracted by Soxhlet extraction, the whole amount of the quaternary ammonium salt type cationic surfactant which chemically bonded and physically adsorbed in the organophilic clay mineral can be determined when the organophilic clay mineral is subjected to DTA-TG measurement.

While not restricted in particular, the amount of the quaternary ammonium salt type cationic surfactant used in the organophilic clay mineral is preferably 60 to 140 milliequivalents (referred to as "meq" in the following) with respect to 100 g of the water-swellable clay mineral. Also, the amount of the nonionic surfactant in the organophilic clay mineral is preferably 5 to 100 g and more preferably 15 to 50 g with respect to 100 g of the water-swellable clay mineral.

Such an organophilic clay mineral is disclosed, for example, in Japanese Examined Patent Publication No. 2-32015 and has been known to be effective in preparing a stable W/O emulsion. However, it has not at all been known to be effective in stabilizing multiple emulsions and, in particular, in preventing their inner oil phase and outer oil phase from combining together.

In an O/W/O type multiple emulsion, when such an organophilic clay mineral is contained in its outer oil phase, its inner oil phase and outer oil phase are prevented from combining together, thereby yielding an O/W/O type multiple emulsion having a very high stability over time. Further, when an oil-soluble agent is compounded in the inner oil phase of such a system, the oil-soluble agent is prevented from being oxidized, whereby an excellent stability of the agent can be obtained.

The amount of the organophilic clay mineral used in the multiple emulsion composition is preferably 0.1 to 5% by weight and more preferably 0.5 to 3% by weight. Below 0.1%, the effects of the addition of the organophilic clay mineral may not be exhibited, whereby a stable multiple emulsion may not be obtained. Specifically, the inner oil phase may disappear over time and thereby the multiple emulsion can not be maintained. Above 5%, on the other hand, practical problems may occur. For example, the prepared emulsion may have high viscosity, low spreadability, roughness, or no transparency.

In the present invention, as the organophilic clay mineral obtained as mentioned above is compounded in the outer oil phase, a wide range of oils from polar oils to nonpolar oils can be used as an oil phase component. Examples of the oils include hydrocarbon oils such as liquid paraffin, squalane, isoparaffin, and branched-chain light paraffin; ester oils such as isopropyl myristate, cetyl isooctanoate, and glyceryl trioctanoate; and silicone type oils.

When a silicone type oil is used, an emulsion having favorable oil resistance, water resistance, and feel of use can be obtained. In the present invention, though a variety of silicone oils can be widely used as a silicone type oil, those having a boiling point of 200° C. or less at normal pressure are preferable from the viewpoint of feel of use and formulation. Examples thereof include a chain polysiloxane such as dimetyhlpolysiloxane, methylphenylpolysiloxane, and methylhydrogenpolysiloxane as well as a cyclopolysiloxane such as decamethylcyclopentasiloxane, dodecamethyl cyclohexasiloxane, and tetramethyltetrahydrogencyclotetrasiloxane. Among them, when a-volatile silicone type oil such as volatile chain polysiloxane or volatile cyclic polysiloxane is used, oily feel is harder to remain when applied to the skin as compared with a normal silicone type oil, whereby it is preferably used when refreshing feel of use is required. Examples of volatile chain polysiloxane include dimethylpolysiloxane having low degree of polymerization (degree of polymerization: 3 to 7), and examples of volatile cyclic polysiloxane include decamethylcyclopentasiloxane and octamethylcyclotetrasiloxane.

In the multiple emulsion of the present invention, though the amount of silicone type oil added therein can be appropriately selected, it is preferably 5% to 60% by weight, particularly preferably 5% to 40% by weight, and further preferably 15% to 40% by weight with respect to the whole multiple emulsion amount. When the amount of silicone type oil added is too less, water resistance, oil resistance, feel of use, and the like may not be obtained sufficiently; whereas, when it is too much, there are cases where it becomes difficult to stabilize the emulsion.

In the present invention, though these silicone type oils can also be added in the inner oil phase, they are preferably added in the outer oil phase. When a silicone type oil is added in the outer oil phase, while the amount of the silicone type oil added with respect to the whole amount of the outer oil phase can be selected within the range of 8% to 100% by weight depending on the ratio of the outer oil phase to the multiple emulsion, it is preferably 60% by weight or more and particularly preferably 90% by weight or more.

According to one of the most preferable embodiments in the O/W/O type multiple emulsion containing a silicone type oil in accordance with the present invention, the inner oil phase is a non-silicone type oil, whereas the outer oil phase is a silicone type oil. Also, according to one of preferable embodiments, the inner oil phase is a non-silicone type oil, whereas the outer oil phase is a mixture of a silicone type oil and a non-silicone type oil.

The hydrophilic polymer in the present invention raises viscosity of the water phase, thereby suppressing coalescence of the inner oil phase and its migration to the outer oil phase. Also, upon use, when the hydrophilic polymer in the water phase is made to gel, the agent dissolved in the inner oil phase can be gradually released. Namely, since the gradually releasing characteristics depends on viscosity of the water phase and the hardness of the gel, the releasing speed can be freely adjusted when the kind of the polymer and the concentration thereof are controlled. For examples of the hydrophilic polymer used, sodium alginate, carageenan, zansan gum, gelatin, cardrant, agar, glucomannan, starch, hyaluronic acid, scleroglucan, syzofiran, renchnum, paramylon, kallose, laminaran, cellulose, methylcellulose, ethylcellulose, nitrocellulose, gum arabic, polyvinyl alcohol, carboxyvinyl polymer, carboxymethylcellulose, hydroxyethylcellulose, polyethylene glycol, tragacanth gum, garactan, guar gum, carob gum, karaya gum, pectin, guince seed, argecolloids, glycyrhizinic acid, dextran, puluran, collagen, casein, albumen, carboxymethyl starch, methylhydroxypropyl starch, methylhydroxypropylcellulose, sodium cellulose sulfate, hydroxypropylcellulose, propylene glycol alginate, polyvinylmethyl ether, polyvinyl pyrrolidone, polyoxyethylene polyoxypropylene copolymer, sodium polyacrylate, polyethylacrylate, polyacryl amide, and polyethlene imine can be cited. In the present invention, one or more can be selected from them.

The method of preparing the O/W type emulsion using the hydrophilic surfactant is not restricted in particular as long as a stable emulsion can be obtained thereby. An example of such a method comprises a first step of adding a hydrophilic nonionic surfactant to a water-soluble solvent and then adding components of an inner oil phase thereto so as to form an oil in water-soluble solvent type emulsion and a second step of adding components of a water phase to this emulsion (e.g., Japanese Examined Patent Publication No. 57-29213). When such an emulsifying technique is used for preparing the O/W type emulsion, the inner oil phase can be compounded minutely and stably. Accordingly, it is particularly preferable for preparing the multiple emulsion in accordance with the present invention.

The water-soluble solvent used in this emulsifying technique dissolves the hydrophilic nonionic surfactant and efficiently makes the surfactant adsorb on the interface with respect to the oil phase which is subsequently added thereto. It can be selected from a very wide range of agents such as lower monohydric alcohols, lower polyhydric alcohols, ketones, aldehydes, ethers, amines, lower fatty acids, and others as long as they are hydrophilic and can dissolve the nonionic surfactant. Specific examples thereof include the water-soluble solvents disclosed in Japanese Examined Patent Publication No. 57-29213.

As the hydrophilic nonionic surfactant, ethylene oxide and/or propylene oxide addition products are preferable. Specific examples thereof include the hydrophilic nonionic surfactants disclosed in Japanese Examined Patent Publication No. 57-29213.

Further, when thus obtained O/W type emulsion is mixed and emulsified in the outer oil phase containing the above-mentioned organophilic clay mineral while being stirred, the aimed O/W/O type multiple emulsion can be obtained. While the emulsifier used at this time is not restricted in particular, disper (TK HOMO DISPER; Tokushu Kika Kogyo Co., Ltd) or the like is preferably used.

Here, the ratio of the O/W type emulsion to the outer oil phase containing the organophilic clay mineral is preferably 2:3 to 19:1 and more preferably 1:1 to 4:1. When the O/W type emulsion has a mixing ratio lower than 2:3, the prepared multiple emulsion may have low viscosity and the emulsification stability may deteriorate over time. On the other hand, when the O/W type emulsion has a mixing ratio greater than 19:1, the phase inversion may occur during emulsification with stirring, thereby failing to form a multiple emulsion.

In the multiple emulsion formed in the foregoing manner, as shown in FIG. 2, an organophilic clay mineral 20 is adsorbed on the interface between a water phase 12 and an outer oil phase 10, whereby an inner oil phase 14 and the outer oil phase 10 are separated from each other by the organophilic clay mineral 20 structurally and physically. As a result, the inner oil phase 14 can be effectively prevented from combining with the outer oil phase 10, thereby attaining an excellent emulsification stability. The effect obtained in the present invention that stability of the agent contained in the inner oil phase to oxidation is improved is considered to be due to the fact that it is hardly possible for the agent to come into direct contact with the outer oil phase or external atmosphere since the oil-soluble agent blended in the inner oil phase at the time of its preparation cannot move to the outer oil phase according to the mechanism explained above. Also, since heating during the preparation step is not required in particular, thermal decomposition during the preparation hardly occurs, whereby it is fully possible for ingredients having a low thermal stability to be added.

Further, for example, when an oil-soluble agent which is hard to dissolve in a silicone type oil content and a polar oil to which the agent has a high solubility are added in the inner oil phase, whereas the silicone type oil is added in the outer oil phase, crystals of the agent can be prevented from depositing while these ingredients can stably coexist in one emulsion system. Also, its feel of use has a favorable spreadability and no greasiness, thereby making it quite superior to simple W/O type emulsions containing a silicone type oil.

The oil-soluble agent used in the present invention can be selected according to the aimed purpose. While it is not restricted in particular as long as it is generally used in cosmetics and medicines, examples thereof include oil-soluble vitamins, oil-soluble ultraviolet absorbers, and unsaturated fatty acids and the derivatives thereof. In particular, easily oxidizable oil-soluble materials are effectively used since their oxidation stability can be improved.

Examples of the oil-soluble vitamins include, as vitamin A group, retinol, 3-dehydroretinol, retinal, 3-dehydroretinal, retinoic acid, 3-dehydroretinoic acid, and esters such as vitamin A acetate and vitamin A palmitate and, as provitamin A, carotenoids and xanthophylls such as α-, β-, and γ-carotenes, β-cryptoxanthin, and echinenone. Examples of vitamin D include vitamin $D_2$ to $D_7$. Examples of vitamins E include α-, β-, γ-, and δ-tocopherols, α-, β-, γ-, and δ-tocotrienols and esters such as vitamin E acetate and vitamin E nicotinate. Examples of vitamin K include vitamin $K_1$ to $K_3$.

Examples of ultraviolet absorbers include benzophenone type ultraviolet absorbers such as 2,4-dihydroxybenzophenone, 2,2'-dihydroxy-4-methoxybenzo phenone, 2,2'-dihydroxy-4,4'-dimethoxybenzophenone, 2,2', 4,4'-tetrahydroxybenzo phenone, 2-hydroxy-4-methoxybenzophenone, 2-hydroxy-4-methoxy-4'-methyl benzophenone and others such as 3-(4'-methylbenzylidene)-d,l-camphor, 3-benzylidene-d,l-camphor, 4-methoxy-4'-t-butylbenzoylmethane. Those which are solid at normal temperature may be dissolved in the oil component and then added.

Examples of unsaturated fatty acids include oleic acid, linoleic acid, α-linolenic acid, γ-linolenic acid, dihomo-γ-linolenic acid, arachidonic acid, eicosapentaenic acid, and docosahexaenic acid. Examples of derivatives thereof include alchol esters such as methyl ester, ethyl ester, and propyl ester; glycerides such as monoglyceride, diglyceride, and triglyceride; phospholipids such as phosphatidylcoline, phosphatidylethanolamine, and sphingomyelin; glycolipids such as glucosylceramide; ceramides; waxs; and esters of cholesterol. In the present invention, when an unsaturated fatty acid having high degree of unsaturation such as that having three or more unsaturated bonds in a molecule is selected from them, its very high stability can be obtained as well.

An oil-soluble agent which is hard to dissolve in a silicone type oil is also preferable as an oil-soluble material in the present invention since it can be prevented from depositing crystals when added in an oil phase different from that containing a silicone type oil as mentioned above. Also, when the agent is a liquid, it can be prevented from separation. Examples of such slightly soluble agents to silicone type oils include, in addition to the above-mentioned ultraviolet absorbers, Antalon (polyvinylpyrrolidone alkyl copolymer), which is used as a film former in sunscreen preparations, and liquid perfumes such as hexenol, 3-octanol, 1-octene-3-ol, 9-deserol, linalool, and geraniol, which are relatively high polar and have low solubility to silicone type oils.

Since the multiple emulsion in accordance with the present invention has excellent stabilities of emulsification and the agent, application in various fields can be expected. In particular, it is usable in cosmetic and medical external preparations for skin such as a milky lotion, a cream, and a foundation. Also, cosmetics for heir such as a shampoo and a rinse can be included.

The multiple emulsion of the present invention can additionally comprise other components which is commonly used in cosmetics and medical external preparations for skin when they will not detract the effects of the present invention. Examples thereof include alcohols, humectants, whitening agents, ultraviolet absorbers, preservatives, cheleting agents, perfumes, coloring agents, pigments, dyes, surfactants, and the other agents.

EXAMPLES

Figure 1:
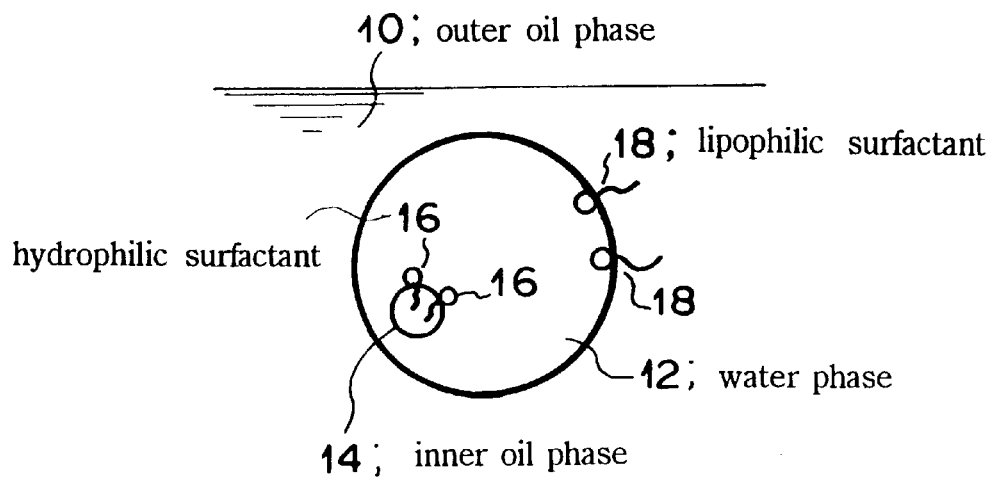
FIG. 1 is a conceptual view showing the conventional O/W/O multiple emulsion and FIG. 2 is a conceptual view showing the O/W/O multiple emulsion in accordance with the present invention.
Figure 2:
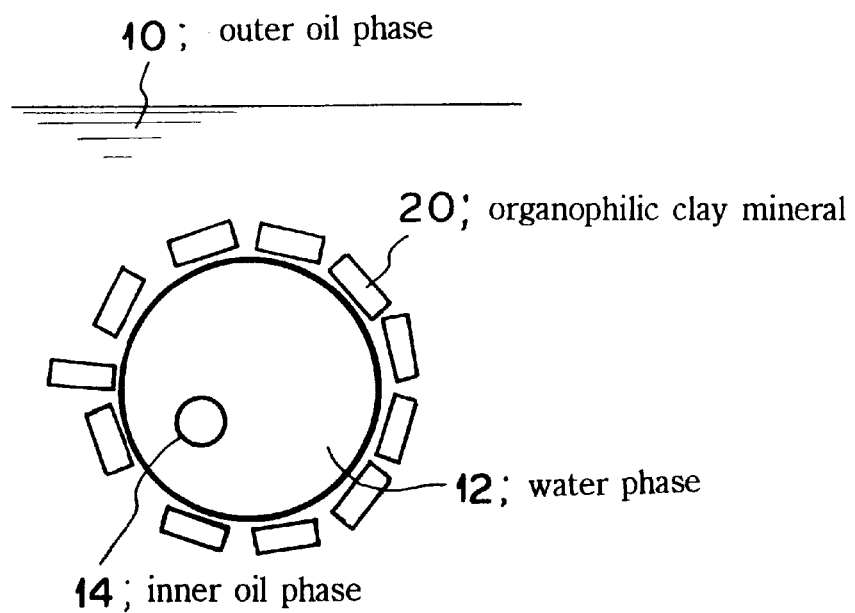

In the following, the present invention will be explained in further detail with reference to specific examples thereof. Here, the present invention is not restricted to these examples. The blending ratio in the following is indicated by % by weight unless otherwise specified.

Preparation of Organophilic Clay Mineral

First, a method of preparing the organophilic clay mineral used in the present invention and a method for confirming it will be explained in detail.

Preparation 1

At 50° C., 45 g of benzyldimethylstearylammonium chloride (corresponding to about 100 meq) and 30 g of POE(6) lauryl ether were dissolved to form 500 ml of an aqueous solution. Then, to this solution, 100 g of Beegum (product name of Vanderbilt Co., USA), namely, a water-swellable clay mineral, were added. The resulting mixture was sufficiently dispersed and mixed for about 30 minutes by a disper. After water was removed by a filter, the residue was dried for about one day and night so as to yield the aimed organophilic clay mineral. In order to judge whether benzyldimethylstearyl ammonium chloride (referred to as "(A)") and POE(6) lauryl ether (referred to as "(B)") had been chemically and physically adsorbed or not, X-ray diffraction was performed as well as the thermal decomposition amount of the surfactant was measured by DTA-TG technique and compared with the water-swellable clay mineral (Beegum).

Table 1 shows the results thereof.

TABLE 1

| Measurement item | Clay mineral before treatment (Beegum) | Organophilic clay mineral of Preparation 1 | |
|---|---|---|---|
| Distance between layers by X-ray diffraction | 13.2 Å | 40.1 Å | |
| Thermal decomposition amount* of the surfactants by DTA-TG | 0 | (A) 101 meq | (B) 29 g |

*Expressed as an amount per 100 g of the water-swellable clay mineral.

As evidenced by Table 1, the distance between layers of the organophilic clay mineral of Preparation 1 is remarkably wider than that of the water-swellable clay mineral before treatment. As can be seen from the results of DTA-TG measurement, it is caused by binding of benzyldimethylstearylammonium chloride (A) and POE(6) lauryl ether (B) to the water-swellable clay mineral.

Preparation 2

In 50 ml of ethanol in which 20 g of POE(15) 2-octyldecyl ether (referred to as "(C)") had been dissolved, 100 g of Benton-38, namely, an organophilic clay mineral, were sufficiently dispersed and mixed by a laboratory homogenizer. Benton-38, a product name of National Red Co., USA, is an organophilic clay mineral formed when 100 g of montmorillonite, namely, a water-swellable clay mineral, were treated with 100 meq of distearyldimethylammonium chloride (referred to as "(D)").

After ethanol was removed by an evaporator, the residue was dried for about one day and night so as to yield the aimed organophilic clay mineral. As in the case of Preparation 1, the X-ray diffraction and the thermal decomposition amount of the surfactant by DTA-TG technique were used to judge whether there had been modification or not. Here, Soxhlet extract of the organophilic clay mineral by chloroform was subjected to DTA-TG measurement as a sample.

Table 2 shows the results thereof.

TABLE 2

| Measurement item | Benton-38 | | Organophilic clay mineral of Preparation 2 | |
|---|---|---|---|---|
| Distance between layers by X-ray diffraction | 26.8 Å | | 36.8 Å | |
| Thermal decomposition amount* of the surfactants in Soxhlet extract by DTA-TG | (D) 12 meq | (C) 0 | (D) 12 meq | (C) 20 g |

*This is the same as Table 1.

As evidenced by Table 2, even when an organophilic clay mineral (Benton-38) which has been treated with quaternary ammonium type cationic surfactant is used, the distance between its layers is further widened when treated with the nonionic surfactant (C). As in the case of Preparation 1, it is considered to be caused by the adsorption of the nonionic surfactant. Here, the amount of the quaternary ammonium salt type cationic surfactant extracted by Soxhlet extraction corresponds to that physically adsorbed in the organophilic clay mineral (Benton-38) which has been organically denatured by cationic exchange reaction, while that chemically bonded in Benton-38 due to cationic exchange cannot be extracted by Soxhlet extraction. As shown in Preparation 1, the whole amount of the quanternary ammonium salt type cationic surfactant which chemically bonded and physically adsorbed in the organophilic clay mineral can be determined by DTA-TG technique measurement of the organophilic clay mineral.

Method of Evaluating Emulsification Stability of Multiple Emulsion

In the examples which will be explained later, the emulsification stability of the multiple emulsion was evaluated as follows:

1) Observation of the Emulsified State

After the emulsion prepared had been kept at room temperature (RT) for six months or at 50° C. in an incubator for one month, its emulsified state was observed by an optical microscope and naked eyes. The case where no abnormality was observed (where emulsion conditions and particles are uniform) was evaluated as good (⊚), the case where no abnormality was observed by naked eyes though slight fluctuation of the particle size was observed by the microscope was evaluated as fair (O), and the case where abnormality was observed (where water or an oil was separated, particles become large, etc) was evaluated as poor (X).

2) Inner Oil Phase Remaining Ratio

This is an experiment for showing that the inner oil phase is not absorbed by the outer oil phase.

i) Qualitative Experiment

An O/W/O type multiple emulsion was prepared and then the change of its state over time was observed by a microscope. In unstable systems, the inner oil phase disappears and the emulsion becomes a simple W/O type emulsion finally. In order to perform an accelerated test, this experiment was effected at a high temperature of 50° C.

ii) Quantitative Experiment

An oil-soluble marker agent (phthalic acid diester) was dissolved in the inner oil phase so as to prepare an O/W/O type multiple emulsion. Then, this emulsion was centrifuged so as to forcibly separate the oils of the outer oil phase. The marker concentration in the outer oil phase was quantitatively determined and then subtracted from the whole concentration to calculate the marker concentration in the inner oil phase. As this process was performed over time, the state of movement of the inner oil phase into the outer oil phase could be observed, thereby calculating the inner oil phase remaining ratio.

Method of Evaluating Agent Stability

1) Agent Remaining Ratio

After sample emulsions were kept at 50° C. in an incubator for one month, the agent concentration in each sample was quantitatively determined by HPLC technique and the remaining ratio (%) of each agent with respect to its charged amount was calculated. According to the remaining ratio, the agent stability was indicated as follows:

⊚: remaining ratio is not lower than 90% with respect to charged amount.

O: remaining ratio is at least 80% but less than 90% with respect to charged amount.

Δ: remaining ratio is at least 60% but less than 80% with respect to charged amount.

X: remaining ratio is less than 60% with respect to charged amount.

2) Crystal Deposit

The samples were stored at 50° C. for a month and then observed whether the agent deposited by light microscope.

O: no crystal deposit is observed(none).

Δ: crystal deposit is slightly observed(slight).

X: crystal deposit is remarkably observed(deposit).

Method of Evaluating Feel of Use

Each of samples prepared was applied on skin of 10 special panels, whereby the feeling test was performed. The result of evaluation was indicated as follows:

⊚: 8 or more panels answered that it was free of greasiness.

O: 6 or 7 panels answered that it was free of greasiness.

Δ: 4 or 5 panels answered that it was free of greasiness.

X: 3 or less panels answered that it was free of greasiness.

EXAMPLE 1

First, the inventors prepared O/W, W/O, and O/W/O type emulsions by conventional techniques with some surfactants according to the prescription shown in Table 3 to Table 5 and evaluated the emulsification stability of the emulsions.

TABLE 3

O/W Type Emulsion

| Constituent | Example 1-1 |
|---|---|
| (a) Surfactant phase | |
| 1,3-Butanediol | 21 |
| Purified water | 2 |
| POE(60) hardened castor oil | 2 |
| (b) Oil phase | |
| Liquid paraffin | 33 |
| (c) Water phase | |
| Purified water | 42 |
| Emulsification stability (observation of the state) | |
| RT | ○ |
| 50° C. | ○ |

<Method of Preparation>

Into a mixture prepared by uniformly dissolved ingredient (a) listed in Table 3, ingredient (b) was mixed and emulsified while being stirred. Then, ingredient (c) was added thereto and mixed therewith to yield an O/W type emulsion.

TABLE 4

W/O Type Emulsion

| | Example | | | | | |
|---|---|---|---|---|---|---|
| Constituent | 1-2 | 1-3 | 1-4 | 1-5 | 1-6 | 1-7 |
| (a) Surfactant | | | | | | |
| POE(3) oleyl ether | 1 | — | — | — | — | — |
| POE(2) oleyl ether | — | 5 | — | — | — | — |
| Sorbitan monostearate | — | — | 1 | — | — | — |
| Sorbitan monostearate | — | — | — | 5 | — | — |
| POE(10) hardened castor oil | — | — | — | — | 10 | — |
| POE(10) hardened castor oil | — | — | — | — | — | 5 |
| (b) Oil phase | | | | | | |
| Liquid paraffin | 39 | 35 | 39 | 35 | 30 | 35 |
| (c) Water phase | | | | | | |
| Ion-exchanged water | 60 | 60 | 60 | 60 | 60 | 60 |
| Emulsification stability (observation of the state) | | | | | | |
| RT | ○ | ○ | ○ | ○ | ○ | ○ |
| 50° C. | ○ | ○ | ○ | ○ | ○ | ○ |

<Method of Preparation>

In Table 4, the above-mentioned ingredients (a) and (b) were mixed and then ingredient (c) was mixed and emulsified therein while being stirred so as to yield the aimed W/O type emulsion.

TABLE 5

O/W/O Type Emulsion

| | Example | | | | | |
|---|---|---|---|---|---|---|
| Constituent | 1-8 | 1-9 | 1-10 | 1-11 | 1-12 | 1-13 |
| (a) O/W phase | | | | | | |
| O/W type emulsion of Example 1-1 | 70 | 70 | 70 | 70 | 70 | 70 |
| (b) Outer oil phase | | | | | | |
| Liquid paraffin | 29 | 25 | 29 | 25 | 20 | 25 |
| (c) Lipophilic surfactant | | | | | | |
| POE(3) oleyl ether | 1 | — | — | — | — | — |
| POE(2) oleyl ether | — | 5 | — | — | — | — |
| Sorbitan monostearate | — | — | 1 | — | — | — |
| Sorbitan monostearate | — | — | — | 5 | — | — |
| POE(10) hardened castor oil | — | — | — | — | 10 | — |
| POE(10) hardened castor oil | — | — | — | — | — | 5 |
| Emulsification stability Observation of the state | | | | | | |
| RT | X | X | X | X | X | X |
| 50° C. | X | X | X | X | X | X |
| Inner oil phase remaining ratio (after 8 weeks at 50° C.) | <5 | <5 | <5 | <5 | <5 | <5 |

<Method of Preparation>

In Table 5, ingredients (b) and (c) were mixed and then the O/W type emulsion (a) of Example 1-1 was mixed and emulsified in the ingredient (b)+(c) while being stirred so as to yield the aimed O/W/O type multiple emulsion.

According to Tables 3 and 4, a considerably high emulsification stability can be attained in O/W type emulsions and W/O type emulsions by selecting appropriate surfactants. However, when a stable O/W emulsion was dispersed in an outer oil phase to form an O/W/O type emulsion, the emulsification stability of thus obtained O/W/O emulsion was greatly deteriorated, whereby the inner oil phase exuded into the outer oil phase.

Therefore, the inventors studied the effect of an organophilic clay mineral on multiple emulsion stabilization and, in particular, the effect on prevention of its inner oil phase and outer oil phase from combining together as follows.

TABLE 6

| | Example | | | | |
|---|---|---|---|---|---|
| Constituent | 1-14 | 1-15 | 1-16 | 1-17 | 1-18 |
| (a) O/W phase | | | | | |
| O/W type emulsion of Example 1-1 | 70 | 70 | 70 | 70 | 70 |
| (b) Outer oil phase | | | | | |
| Liquid paraffin | 28 | 28 | 28 | 28 | 28 |
| (c) Surfactant in outer oil phase | | | | | |
| Organophilic clay mineral (Preparation 1) | 2 | — | — | — | — |
| Unmodified clay mineral(Beegum) | — | 2 | — | — | — |
| Benzyldimethylstearyl ammonium chloride | — | — | 2 | — | — |
| POE(6) lauryl ether | — | — | — | 2 | — |
| Benzyldimethylstearylammonium chloride + POE(6) lauryl ether | — | — | — | — | 2 |
| Emulsification stability | | | | | |

TABLE 6-continued

| Constituent | Example | | | | |
|---|---|---|---|---|---|
| | 1-14 | 1-15 | 1-16 | 1-17 | 1-18 |
| Observation of the state | | | | | |
| RT | ○ | X | X | X | X |
| 50° C. | ○ | X | X | X | X |
| Inner oil phase remaining ratio (after 8 weeks at 50° C.) | 98 | <5 | <5 | <5 | <5 |

<Method of Preparation>

In a manner similar to the method of Table 5 shown above, the O/W/O type multiple emulsion was prepared by the prescription shown in Table 6.

As can be seen from Table 6, when the organophilic clay mineral was compounded in the outer oil phase, an emulsion which was quite good in both stability of the emulsification state and inner oil phase remaining ratio was obtained.

On the other hand, when the unmodified clay mineral, benzyldimethylstearyl ammonium chloride, and POE (6) lauryl ether, which were constituents of the organophilic clay mineral, were used separately or in combination, the high emulsification stability such as those obtained when the organophilic clay was compounded could not obtained.

Accordingly, it is understood that the effect of the organophilic clay mineral on the stability of the multiple emulsion is specific and that the emulsification stability of the multiple emulsion cannot be improved when the stable O/W type emulsion is simply substituted for a water phase of the stable W/O type emulsion.

EXAMPLE 2

Next, a preferable composition of the multiple emulsion of the present invention was studied.

(1) Composition

TABLE 7

Composition of O/W Type Emulsion

| Constituent | Content |
|---|---|
| (a) Surfactant phase | |
| 1,3-Butanediol | 21 |
| Purified water | 2 |
| POE(60) hardened castor oil | 2 |
| (b) Inner oil phase | |
| Liquid paraffin | 33 |
| (c) Water phase | |
| Purified water | 42 |

TABLE 8

Composition of Outer oil phase

| Constituent | Content |
|---|---|
| (d) Surfactant | |
| Organophilic clay mineral of Preparation 1 | 7 |
| (e) Outer phase oil | |
| Liquid paraffin | 93 |

TABLE 9

Constitutional Ratio of O/W/O Type Multiple Emulsion

| Example | Amount of O/W type emulsion (parts by weight) | Amount of outer oil phase (parts by weight) |
|---|---|---|
| Example 2-1 | 50 | 50 |
| Example 2-2 | 60 | 40 |
| Example 2-3 | 70 | 30 |
| Example 2-4 | 80 | 20 |
| Example 2-5 | 35 | 65 |
| Example 2-6 | 97 | 3 |

(2) Method of preparation

First, into the mixture of uniformly dissolved ingredient (a) shown in Table 7, ingredient (b) was mixed and emulsified while being stirred. Then, ingredient (c) was added thereto and mixed therewith to yield an O/W type emulsion.

Thereafter, the outer oil phase component shown in Table 8 was mixed. In this outer oil phase, the O/W type emulsion prepared above was mixed and emulsified while being stirred to yield the aimed O/W/O type multiple emulsion. Here, the ratio of the O/W type emulsion to the outer oil phase was changed as shown in Table 9 to form Examples 2-1 to 2-6.

(3) Result

TABLE 10

Evaluation of Emulsion Characteristics

| Outer oil phase | Emulsion form directly after preparation | Emulsification stability | | Inner oil phase remaining ratio* (50° C., 1 month) |
|---|---|---|---|---|
| | | RT | 50° C. | |
| Ex. 2-1 | O/W/O | ○ | ○ | 93.0% |
| Ex. 2-2 | O/W/O | ⊙ | ○ | 95.5 |
| Ex. 2-3 | O/W/O | ⊙ | ⊙ | 98.6 |
| Ex. 2-4 | O/W/O | ⊙ | ○ | 92.8 |
| Ex. 2-5 | O/W/O | X | X | — |
| Ex. 2-6 | O/W/O + O/W | X | X | — |

As can be seen from Table 10, since the amount of the outer oil phase was greater than the ratio expressed by the O/W type emulsion to the outer oil phase ratio of 2:3, while an O/W/O type emulsion was formed directly after the emulsification, Example 2-5 exhibited an inferior emulsification stability as compared with Examples 2-1 to 2-4, whereby floating of oil was recognized in both of room temperature storage and 50° C. storage. Also, as shown in Example 2-6, when the O/W type emulsion was greater than the ratio expressed by the O/W type emulsion to the outer oil phase ratio of 19:1, phase inversion occurred during emulsification and dispersion, whereby it was confirmed that the O/W/O and O/W types coexisted in the emulsion prepared.

Accordingly, the ratio of O/W type emulsion to the outer oil phase is within the range of 2:3 to 19:1, preferably.

COMPARATIVE EXAMPLE 1

Outer oil phases were prepared according to compositions of Comparative Examples 1-1 to 1-6 shown in the following Table 11. In each outer oil phase, the lipophilic surfactant commonly used for preparing the conventional W/O type emulsion was used therein.

Further, an O/W type emulsion prepared in a manner similar to Table 7 of Example 2 and each of the outer oil phases of Comparative Examples shown in Table 11 were mixed and emulsified together at a ratio of 7:3 by weight.

The emulsification stability of thus prepared emulsion was evaluated in a manner similar to Example 2.

TABLE 11

Composition of Outer Oil Phase

| Outer oil phase | Lipophilic surfactant (parts by weight) | Oil (parts by weight) |
| --- | --- | --- |
| Comp. Ex. 1-1 | POE(3)oleyl ether (1) | liquid paraffin (99) |
| Comp. Ex. 1-2 | POE(3)oleyl ether (5) | liquid paraffin (95) |
| Comp. Ex. 1-3 | sorbitan monostearate (1) | liquid paraffin (99) |
| Comp. Ex. 1-4 | sorbitan monostearate (5) | liquid paraffin (95) |
| Comp. Ex. 1-5 | POE(10) hardened castor oil (10) | liquid paraffin (90) |
| Comp. Ex. 1-6 | POE(10) hardened castor oil (5) | liquid paraffin (95) |

TABLE 12

Evaluation of Emulsion Characteristics

| Outer oil phase | Emulsion form directly after preparation | Emulsion stability RT | 50° C. |
| --- | --- | --- | --- |
| Comp. Ex. 1-1 | O/W/O | X | X |
| Comp. Ex. 1-2 | O/W/O + O/W | X | X |
| Comp. Ex. 1-3 | O/W/O | X | X |
| Comp. Ex. 1-4 | O/W/O | X | X |
| Comp. Ex. 1-5 | O/W/O + O/W | X | X |
| Comp. Ex. 1-6 | O/W/O + O/W | X | X |

When the evaluation of Examples shown in Table 10 and that of Comparative Examples shown in Table 12 are compared with each other, it can be seen that Examples 2-1 to 2-4 of the present invention are superior in emulsification stability to Comparative Examples 1-1 to 1-6.

EXAMPLE 3

Further, the inventors studied the emulsification stability and agent stability when an oil-soluble agent was added in the emulsion. Here, as the oil-soluble agent, retinol was used. Each of the preparation methods in Table 13 to 16 was similar to Table 3 to 6 above, respectively.

TABLE 13

O/W Type Emulsion

| Constituent | Example 3-1 |
| --- | --- |
| (a) Surfactant phase | |
| 1,3-Butanediol | 21 |
| Purified water | 2 |
| POE(60) hardened castor oil | 2 |
| (b) Oil phase | |
| Liquid paraffin | 32 |
| Retinol | 1 |
| (c) Water phase | |
| Purified water | 42 |
| Emulsification stability (observation of the state) | |
| RT | ◯ |
| 50° C. | ◯ |
| Agent remaining ratio | X |

TABLE 14

W/O Type Emulsion

| Constituent | Example 3-2 | 3-3 | 3-4 | 3-5 | 3-6 | 3-7 |
| --- | --- | --- | --- | --- | --- | --- |
| (a) Surfactant | | | | | | |
| POE(3) oleyl ether | 1 | — | — | — | — | — |
| POE(2) oleyl ether | — | 5 | — | — | — | — |
| Sorbitan monostearate | — | — | 1 | — | — | — |
| Sorbitan monostearate | — | — | — | 5 | — | — |
| POE(10) hardened castor oil | — | — | — | — | 10 | — |
| POE(10) hardened castor oil | — | — | — | — | — | 5 |
| (b) Oil phase | | | | | | |
| Liquid paraffin | 38 | 34 | 38 | 34 | 29 | 34 |
| Retinol | 1 | 1 | 1 | 1 | 1 | 1 |
| (c) Water phase | | | | | | |
| Ion-exchanged water | 60 | 60 | 60 | 60 | 60 | 60 |
| Emulsification stability (observation of the state) | | | | | | |
| RT | ◯ | ◯ | ◯ | ◯ | ◯ | ◯ |
| 50° C. | ◯ | ◯ | ◯ | ◯ | ◯ | ◯ |
| Agent remaining ratio | X | X | X | X | X | X |

TABLE 15

O/W/O Type Emulsion

| Constituent | Example 3-8 | 3-9 | 3-10 | 3-11 | 3-12 | 3-13 |
| --- | --- | --- | --- | --- | --- | --- |
| (a) O/W phase (containing retinol in oil phase) | | | | | | |
| O/W type emulsion of Example 3-1 | 70 | 70 | 70 | 70 | 70 | 70 |
| (b) Outer oil phase | | | | | | |
| Liquid paraffin | 29 | 25 | 29 | 25 | 20 | 25 |
| (c) Lipophilic surfactant | | | | | | |
| POE(3) oleyl ether | 1 | — | — | — | — | — |
| POE(2) oleyl ether | — | 5 | — | — | — | — |
| Sorbitan monostearate | — | — | 1 | — | — | — |
| Sorbitan monostearate | — | — | — | 5 | — | — |
| POE(10) hardened castor oil | — | — | — | — | 10 | — |
| POE(10) hardened castor oil | — | — | — | — | — | 5 |
| Emulsification stability Observation of the state | | | | | | |
| RT | X | X | X | X | X | X |
| 50° C. | X | X | X | X | X | X |
| Inner oil phase remaining ratio (after 8 weeks at 50° C.) | <5 | <5 | <5 | <5 | <5 | <5 |
| Agent remaining ratio | X | X | X | X | X | X |

TABLE 16

O/W/O type multiple emulsion

| Constituent | Example 3-14 | 3-15 | 3-16 | 3-17 | 3-18 |
| --- | --- | --- | --- | --- | --- |
| (a) O/W phase (containing retinol in oil phase) | | | | | |
| O/W type emulsion | 70 | 70 | 70 | 70 | 70 |

TABLE 16-continued

O/W/O type multiple emulsion

| Constituent | Example 3-14 | 3-15 | 3-16 | 3-17 | 3-18 |
|---|---|---|---|---|---|
| of Example 3-1 | | | | | |
| (b) Outer oil phase | | | | | |
| Liquid paraffin | 28 | 28 | 28 | 28 | 28 |
| (c) Surfactant in outer oil phase | | | | | |
| Organophilic clay mineral (Preparation 1) | 2 | — | — | — | — |
| Unmodified clay mineral(Beegum) | — | 2 | — | — | — |
| Benzyldimethylstearyl ammonium chloride | — | — | 2 | — | — |
| POE(6) lauryl ether | — | — | — | 2 | — |
| Benzyldimethylstearyl ammonium chloride + POE(6) lauryl ether | — | — | — | — | 2 |
| Emulsification stability Observation of the state | | | | | |
| RT | ○ | X | X | X | X |
| 50° C. | ○ | X | X | X | X |
| Inner oil phase remaining ratio (after 8 weeks at 50° C.) | 98 | <5 | <5 | <5 | <5 |
| Agent remaining ratio | ⊚ | X | X | X | X |

According to Tables 13 and 14, while a considerably high emulsification stability can be attained in O/W type emulsions and W/O type emulsions by selecting appropriate surfactants even when an oil-soluble agent is compounded in their oil phase, their agent remaining ratio is quite low. Then, while a stable O/W emulsion was dispersed in the oil phase to form an O/W/O type emulsion in anticipation of an improved agent stability, the emulsification stability of thus obtained O/W/O emulsion was greatly deteriorated, whereby the inner oil phase exuded into the outer oil phase. Thus, retinol added in the inner oil phase exuded into the outer oil phase, whereby anticipated stabilizing effects could not be obtained.

Contrary to this, as can be seen from Table 16, when the organophilic clay mineral was added in the outer oil phase, an emulsion which was quite good in both of stability of the emulsification state and inner oil phase remaining ratio was obtained, and further the agent stability of retinol added in the inner oil phase was remarkably improved.

On the other hand, when the unmodified clay mineral, benzyldimethylstearyl ammonium chloride, and POE (6) lauryl ether, which were constituents of the organophilic clay mineral, were used separately or in combination, the high emulsification stability and agent stability such as those obtained when the organophilic clay was compounded could not be obtained.

Accordingly, when the stable O/W type emulsion is simply substituted for a water phase of the stable W/O type emulsion, the emulsification stability of the multiple emulsion and the stability of the agent added in the inner oil phase cannot be improved. Therefor, it is understood that such effects can be obtained specially only when the organophilic clay mineral is used.

EXAMPLE 4

A preferable composition in cases where an oil-soluble agent was added in the inner oil phase was studied as follows:

(1) Composition

TABLE 17

Composition of O/W Type Emulsion

| Constituent | Content |
|---|---|
| (a) Surfactant phase | |
| 1,3-Butanediol | 21 |
| Purified water | 2 |
| POE(60) hardened castor oil | 2 |
| (b) Inner oil phase | |
| Liquid paraffin | 32 |
| Retinol | 1 |
| (c) Water phase | |
| Purified water | 42 |

TABLE 18

Composition of Outer oil phase

| Constituent | Content |
|---|---|
| (d) Surfactant | |
| Organophilic clay mineral of Preparation 1 | 7 |
| (e) Outer phase oil | |
| Liquid paraffin | 93 |

TABLE 19

Constitutional Ratio of O/W/O Type Multiple Emulsion

| Example | Amount of O/W type emulsion (parts by weight) | Outer oil phase (parts by weight) |
|---|---|---|
| Example 4-1 | 50 | 50 |
| Example 4-2 | 60 | 40 |
| Example 4-3 | 70 | 30 |
| Example 4-4 | 80 | 20 |
| Example 4-5 | 35 | 65 |
| Example 4-6 | 97 | 3 |

(2) Method of preparation

The preparation method was similar to Example 2 above. Namely, first, into the mixture of uniformly dissolved ingredient (a) shown in Table 17, ingredient (b) was mixed and emulsified while being stirred. Then, ingredient (c) was added thereto and mixed therewith to yield an O/W type emulsion.

Thereafter, the outer oil phase components shown in Table 18 were mixed. In this outer oil phase, the O/W type emulsion prepared above was mixed and emulsified while being stirred to yield the aimed O/W/O type multiple emulsion. Here, the ratio of the O/W type emulsion to the outer oil phase was changed as shown in Table 19 to form Examples 4-1 to 4-6.

(3) Result

TABLE 20

Evaluation of Emulsion Characteristics

| Outer oil phase | Emulsion form directly after preparation | Emulsification stability RT | 50° C. | Inner oil phase remaining ratio* | Agent remaining ratio |
|---|---|---|---|---|---|
| Ex. 4-1 | O/W/O | ○ | ○ | 93% | ◉ |
| Ex. 4-2 | O/W/O | ◉ | ○ | 96 | ◉ |
| Ex. 4-3 | O/W/O | ◉ | ◉ | 99 | ◉ |
| Ex. 4-4 | O/W/O | ◉ | ○ | 93 | ◉ |
| Ex. 4-5 | O/W/O | X | X | — | X |
| Ex. 4-6 | O/W/O + O/W | X | X | — | X |

*Inner oil remaining ratio was measured after the storage at 50° C. for one month.

As can be seen from Table 20, when the ratio of O/W type emulsion to outer oil phase is outside of the range of 2:3 to 19:1, stable multiple emulsions cannot be obtained and the stability of the agent (retinol) becomes quite unfavorable. Contrary to this, it can be understood that, when the ratio is within the range of 2:3 to 19:1, the system has a favorable emulsification stability and the stability of the agent added in the inner oil phase can be remarkably improved.

EXAMPLE 5

O/W/O type emulsions were prepared in a manner similar to the preparation method of the above-mentioned Example 4, while the amounts of the respective ingredients were changed according to the prescriptions shown in Tables 21 and 22. As a result, it was evidenced that, as in the case of Table 20, the system has favorable emulsification stability and agent stability when the ratio of O/W type emulsion to outer oil phase is within the range of 2:3 to 19:1 by weight ratio.

TABLE 21

Study of Composition Ratio

| Constituent | 5-1 | 5-2 | 5-3 | 5-4 | 5-5 |
|---|---|---|---|---|---|
| (a) Surfactant | | | | | |
| 1,3-Butyleneglycol | 3 | 4 | 3 | 2 | 3 |
| Glycerine | 5 | 6 | 5 | 4 | 5 |
| POE(60) hardened castor oil | 1 | 1.2 | 1 | 0.8 | 1 |
| Methyl paraben | 0.15 | 0.15 | 0.15 | 0.15 | 0.15 |
| (b) Inner oil phase | | | | | |
| Squalane | 5 | 5 | 5 | 5 | 5 |
| Glyceryl tri-2-ethylhexanoate | 5 | 10 | 5 | 2.5 | 5 |
| Vitamin A palmitate | 1 | 2 | 1 | 0.5 | 1 |
| (c) Water phase | | | | | |
| Purified water | 75.35 | 55.15 | 46.85 | 35.55 | 13.85 |
| (d) Outer oil phase | | | | | |
| Squalane | 3 | 15 | 30 | 45 | 60 |
| Cationic denatured clay mineral (Benton-38) | 0.5 | 0.5 | 1 | 1.5 | 2 |
| POE(6) oleyl ether | 1 | 1 | 2 | 3 | 4 |
| O/W emulsion:outer oil phase (weight ratio) | 21:1 | 5:1 | 2:1 | 1:1 | 0.5:1 |
| Emulsification stability (observation of the state) | | | | | |
| 50° C. | X | ○ | ◉ | ○ | X |

TABLE 21-continued

Study of Composition Ratio

| Constituent | 5-1 | 5-2 | 5-3 | 5-4 | 5-5 |
|---|---|---|---|---|---|
| Remaining ratio of vitamin A palmitate | X | ◉ | ◉ | ◉ | X |

TABLE 22

| Constituent | 5-6 | 5-7 | 5-8 | 5-9 | 5-10 |
|---|---|---|---|---|---|
| (a) Surfactant | | | | | |
| 1,3-Butyleneglycol | 3 | 4 | 3 | 2 | 3 |
| Glycerine | 5 | 6 | 5 | 4 | 5 |
| POE(60) hardened castor oil | 1 | 1.2 | 1 | 0.8 | 1 |
| Methyl paraben | 0.15 | 0.15 | 0.15 | 0.15 | 0.15 |
| (b) Inner oil phase | | | | | |
| Octyl methoxycinnamate | 5 | 5 | 5 | 5 | 5 |
| Glyceryl tri-2-ethylhexanoate | 5 | 10 | 5 | 2.5 | 5 |
| Octyl dimethyl PABA* | 1 | 2 | 1 | 0.5 | 1 |
| (c) Water phase | | | | | |
| Purified water | 75.35 | 55.15 | 46.85 | 35.55 | 13.85 |
| (d) Outer oil phase | | | | | |
| Liquid paraffin | 1.5 | 7.5 | 15 | 22.5 | 30 |
| Isoparaffin | 1.5 | 7.5 | 15 | 22.5 | 30 |
| Cationic denatured clay mineral (Benton-38) | 0.5 | 0.5 | 1 | 1.5 | 2 |
| POE(10) oleyl ether | 1 | 1 | 2 | 3 | 4 |
| O/W emulsion:outer oil phase (weight ratio) | 21:1 | 5:1 | 2:1 | 1:1 | 0.5:1 |
| Emulsification stability (observation of the state) | | | | | |
| 50° C. | X | ○ | ◉ | ○ | X |
| Remaining ratio of Octyl dimethyl PABA | X | ◉ | ◉ | ◉ | X |

*Octyl dimethyl PABA; Octyl p-dimethylaminobenzoate.

EXAMPLE 6 AND COMPARATIVE EXAMPLE 2 TO 3

Next, O/W/O type and W/O type emulsions were prepared according to prescriptions shown in Table 23 and their agent stability was studied while the oil-soluble agent added in their inner oil phase was changed.

(1) Composition

TABLE 23

| Constituent | Ex. 6 (O/W/O) | Comp. Ex. 2 (W/O) | Comp. Ex. 3 (O/W/O) |
|---|---|---|---|
| (a) Surfactant phase | | | |
| 1,3-Butyleneglycol | 5 | 5 | 5 |
| POE(60) hardened castor oil | 1 | — | — |
| Bentonite | — | — | 0.5 |
| Methyl paraben | 0.1 | 0.1 | 0.1 |
| (b) Inner oil phase | | | |
| Squalane | 5 | — | 5 |
| Pentaerythritol tetra-2-ethylhexanoate | 5 | — | 5 |
| Cetanol | — | — | 3 |

TABLE 23-continued

| Constituent | Ex. 6 (O/W/O) | Comp. Ex. 2 (W/O) | Comp. Ex. 3 (O/W/O) |
|---|---|---|---|
| POE(20) sorbitan tristearate | — | — | 1 |
| Diglycenne monooleate | — | — | 2 |
| Oil-soluble vitamin(cf. Table 24) | 1 | — | 1 |
| (c) Water phase | | | |
| Purified water | 49.9 | 50.9 | 37.4 |
| (d) Outer oil phase | | | |
| Liquid paraffin | 30 | 30 | 30 |
| Organophilic clay mineral (Preparation 1) | 1 | 1 | 1 |
| POE(6) oleyl ether | 2 | 2 | — |
| Squalane | — | 5 | — |
| Pentaerythritol tetra-2-ethylhexanoate | — | 5 | — |
| Dextrin palmitate | — | — | 1 |
| Cetanol | — | — | 3 |
| Beeswax | — | — | 2 |
| Sorbitan sesquioleate | — | — | 3 |
| Sorbitan monostearate | — | — | 1 |
| Oil-soluble vitamin(cf. Table 24) | — | 1 | — |

(2) Method of Preparation

EXAMPLE 6

To a mixture of uniformly dissolved ingredient (a), ingredient (b) was mixed while being stirred, and the obtained mixture was dispersed and emulsified to yield an oil in surfactant phase type emulsion composition. Then, ingredient (c) was added thereto and mixed therewith to obtain an O/W type emulsion. Thus O/W type emulsion was mixed and emulsified in ingredient (d) which had been mixed and dispersed beforehand, thereby yielding the aimed O/W/O type multiple emulsion.

COMPARATIVE EXAMPLE 2

After ingredient (a) were uniformly dissolved and mixed, ingredients (a) and (c) were mixed. While being stirred, ingredient (a)+(c) was mixed and emulsified in ingredient (d), thereby yielding the aimed W/O type multiple emulsion.

COMPARATIVE EXAMPLE 3

After ingredient (a)+(c) and ingredient (d) were separately heated and melted at 70° C., ingredient (b) was mixed, dispersed, and emulsified in ingredient (a)+(c) while being stirred, thereby yielding an O/W type emulsion. Then, this O/W type emulsion was mixed in ingredient (d), which had been heated and melted at 80° C. beforehand while being stirred, and then cooled to 30° C. while being stirred, thereby yielding the aimed O/W/O type multiple emulsion.

(3) Method of Evaluation

The emulsification stability and agent remaining ratio of thus prepared emulsion were evaluated in the above-mentioned manner. Also, discoloring and change in odor of the emulsion after being kept at 50° C. in an incubator for one month were judged and evaluated according to the following standards.

Discoloring (by visual judgment)
  ⊚: no discoloring
  O: slight discoloring
  Δ: considerable discoloring
  X: remarkable discoloring Change in odor
  ⊚: no change
  O: little change
  Δ: slight offensive odor
  X: remarkable offensive odor (4) Result

TABLE 24

Evaluation of Emulsion Characteristics

| Example | | Oil-soluble vitamin | Emulsification stability | | | Remaining ratio of Vitamin(%) |
|---|---|---|---|---|---|---|
| | | | Discoloring | Odor | State | |
| Example (O/W/O) | 6-1 | retinol | ⊚ | ⊚ | O | 90.5 |
| | 6-2 | vitamin A palmitate | ⊚ | ⊚ | O | 98.1 |
| | 6-3 | vitamin A acetate | ⊚ | ⊚ | O | 97.8 |
| | 6-4 | α-tocopherol | ⊚ | ⊚ | O | 97.2 |
| | 6-5 | vitamin E acetate | ⊚ | ⊚ | O | 100.2 |
| | 6-6 | vitamin $D_2$ | ⊚ | ⊚ | O | 99.5 |
| | 6-7 | β-carotene | ⊚ | ⊚ | O | 96.5 |
| Comp. Ex. (W/O) | 2-1 | retinol | X | X | O | 65.0 |
| | 2-2 | vitamin A palmitate | Δ | Δ | O | 70.1 |
| | 2-3 | vitamin Acetate | Δ | Δ | O | 74.9 |
| | 2-4 | α-tocopherol | Δ | O | O | 69.9 |
| | 2-5 | vitamin E acetate | O | O | O | 80.1 |
| | 2-6 | vitamin $D_2$ | Δ | O | O | 83.8 |
| | 2-7 | β-carotene | Δ | O | O | 79.8 |
| Comp. Ex. (O/W/O) | 3-1 | retinol | X | X | X | 17.2 |
| | 3-2 | vitamin A palmitate | X | X | X | 36.6 |
| | 3-3 | vitamin A acetate | X | X | X | 40.8 |
| | 3-4 | α-tocopherol | Δ | Δ | X | 66.7 |
| | 3-5 | vitamin E acetate | Δ | Δ | X | 78.9 |
| | 3-6 | vitamin $D_2$ | Δ | Δ | X | 80.7 |
| | 3-7 | β-carotene | Δ | O | Δ | 77.7 |

As can be seen from Table 24, the O/W/O type emulsions (Examples 6-1 to 6-7) in which an organophilic clay mineral had been added in the outer oil phase were excellent in emulsification stability without separation of oil or the like, discoloring, and change in odor and exhibited a remarkably high agent remaining ratio.

In the W/O type emulsions of Comparative Examples 2-1 to 2-7, on the other hand, while stable emulsification conditions were obtained without noticeable separation of the oil phase or the like, since the agent (oil-soluble vitamin)

was added in the outer oil phase, the remaining ratio of the agent was remarkably decreased due to the oxidative decomposition. Also, in the O/W/O type multiple emulsions prepared by the conventional technique such as those of Comparative Examples 3-1 to 3-7, their emulsification stability was so low that they were easily separated and, since its preparation step was accompanied by heating, the decomposition of the agent added in the inner oil phase was remarkable and the degree of discoloring and change in odor was great also.

EXAMPLE 7 AND COMPARATIVE EXAMPLE 4

O/W/O type or W/O type emulsions in which various kinds of oil-soluble ultraviolet absorbers were added in the inner oil phase were prepared according to the prescription shown in Table 25 and their emulsification stabilities were studied.

(1) Composition

TABLE 25

| Constituent | Ex. 7 (O/W/O) | Comp. Ex. 4 (W/O) |
|---|---|---|
| (a) Surfactant phase | | |
| 1,3-Butyleneglycol | 5 | 5 |
| POE(60) hardened castor oil | 1 | — |
| Methyl paraben | 0.1 | 0.1 |
| (b) Inner oil phase | | |
| Squalane | 5 | — |
| Pentaerythritol tetra-2-ethylhexanoate | 5 | — |
| Ultraviolet absorber(cf. Table 26) | 2 | — |
| (c) Water phase | | |
| Purified water | 48.9 | 59.9 |
| (d) Outer oil phase | | |
| Liquid paraffin | 30 | 30 |
| Organophilic clay mineral of Preparation 1 | 1 | 1 |

TABLE 25-continued

| Constituent | Ex. 7 (O/W/O) | Comp. Ex. 4 (W/O) |
|---|---|---|
| POE(6) stearyl ether | 2 | 2 |
| Ultraviolet absorber(cf. Table 26) | — | 2 |

(2) Method of preparation
EXAMPLE 7
It was prepared in a manner similar to Example 6.
COMPARATIVE EXAMPLE 4
It was prepared in a manner similar to Comparative Example 2.
(3) Method of evaluation
With respect to the emulsions shown in Table 25, observation of the emulsified state was performed by the above-mentioned method, whereby changes in emulsification conditions such as change in particle size, separation, and discoloring were inspected so as to evaluate the emulsification stability. Here, the storage period was six months at 25° C. or two months at 50° C.
(4) Result

TABLE 26

Emulsification Stability

| Example | | Ultraviolet absorber | Emulsification stability |
|---|---|---|---|
| Example (O/W/O) | 7-1 | 2,4-dihydroxybenzophenone | ⊚ |
| | 7-2 | 2,2'-dihydroxy-4-methoxybenzophenone | ⊚ |
| | 7-3 | 2,2'-dihydroxy-4,4-dimethoxybenzophenone | ⊚ |
| | 7-4 | 2,2',4,4'-tetrahydroxybenzophenone | ⊚ |
| | 7-5 | 2-hydroxy-4-methoxybenzophenone | ⊚ |
| | 7-6 | 2-hydroxy-4-methoxy-4'-methylbenzopheone | ⊚ |
| | 7-7 | 3-(4-methylbenzylidene)-d,1-camphor | ⊚ |
| | 7-8 | 3-benzylidene-d,1-camphor | ⊚ |
| | 7-9 | 4-methoxy-4'-t-butyldibenzoylmethane | ⊚ |
| Comp. Ex. (W/O) | 4-1 | 2,4-dihydroxybenzophenone | X |
| | 4-2 | 2,2'-dihydroxy-4-methoxybenzophenone | X |
| | 4-3 | 2,2'-dihydroxy-4,4-dimethoxybenzophenone | X |
| | 4-4 | 2,2',4,4'-tetrahydroxybenzophenone | X |
| | 4-5 | 2-hydroxy-4-methoxybenzophenone | X |
| | 4-6 | 2-hydroxy-4-methoxy-4'-methylbenzophenone | X |
| | 4-7 | 3-(4-methylbenzylidene)-d,1-camphor | X |
| | 4-8 | 3-benzylidene-d,1-camphor | X |
| | 4-9 | 4-methoxy-4'-t-butyldibenzoylmethane | X |

As can be seen from Table 26, while discoloring, separation of oil, or the like were recognized in the W/O type emulsions of Comparative Examples since the ultraviolet absorbers were contained in the outer oil phase which comes into direct contact with the air, emulsion stability was favorable in any of Examples.

Thus, suncare cosmetic preparations having excellent emulsification stability can be made by using the O/W/O type emulsion in accordance with the present invention.

EXAMPLE 8 AND COMPARATIVE EXAMPLE 5 TO 6

Next, O/W/O type and W/O type emulsions were prepared according to prescriptions shown in Table 27 and their agent stability was studied while the unsaturated fatty acids added in their inner oil phase was changed.

(1) Composition

TABLE 27

| Constituent | Ex. 8 (O/W/O) | Comp. Ex. 5 (W/O) | Comp. Ex. 6 (O/W) |
|---|---|---|---|
| (a) Surfactant phase | | | |
| 1,3-Butyleneglycol | 10 | 10 | 10 |
| POE(60) hardened castor oil | 1 | — | 1 |
| Methyl paraben | 0.1 | 0.1 | 0.1 |
| (b) Inner oil phase | | | |
| Liquid paraffin | 5 | — | 5 |
| Pentaerythritol tetra-2-ethylhexanoate | 5 | — | 5 |
| Cetanol | — | — | 2 |
| Unsaturated fatty acid (cf. Table 28) | 1 | — | 1 |
| (c) Water phase | | | |
| Purified water | 46.9 | 57.9 | 75.9 |

TABLE 27-continued

| Constituent | Ex. 8 (O/W/O) | Comp. Ex. 5 (W/O) | Comp. Ex. 6 (O/W) |
|---|---|---|---|
| (d) Outer oil phase | | | |
| Liquid paraffin | 10 | 10 | — |
| Isoparaffin | 10 | 10 | — |
| Squalane | 10 | 10 | — |
| Organophilic clay mineral (Preparation 1) | 1 | 1 | — |
| Unsaturated fatty acid (cf. Table 28) | — | 1 | — |

(2) Method of preparation

EXAMPLE 8

It was prepared in a manner similar to Example 6.

COMPARATIVE EXAMPLE 5

It was prepared in a manner similar to Comparative Example 2.

COMPARATIVE EXAMPLE 6

To a mixture of uniformly dissolved ingredient (a), ingredient (b) was mixed while being stirred, and the obtained mixture was dispersed and emulsified to yield an oil in surfactant phase type emulsion composition. Then, ingredient (c) was added therein and mixed to yield the O/W type emulsion.

(3) Method of evaluation

It was evaluated in a manner similar to Example 6.

(4) Result

TABLE 28

Evaluation of Emulsion Characteristics

| Example | | Unsaturated fatty acid | Emulsification stability | | | Remaining ratio of Vitamin(%) |
|---|---|---|---|---|---|---|
| | | | Discoloring | Odor | State | |
| Example (O/W/O) | 8-1 | γ-linolenic acid | ◉ | ◉ | ○ | 98.1 |
| | 8-2 | arachidonic acid | ◉ | ◉ | ○ | 94.5 |
| | 8-3 | eicosapentaenic acid | ◉ | ◉ | ○ | 92.1 |
| | 8-4 | docosahexaenic acid | ◉ | ◉ | ○ | 90.2 |
| | 8-5 | methyl docosahexaenate | ◉ | ◉ | ○ | 97.8 |
| | 8-6 | ethyl docosahexaenate | ◉ | ◉ | ○ | 99.2 |
| Comp. Ex. (W/O) | 5-1 | γ-linolenic acid | ○ | Δ | ◉ | 60.9 |
| | 5-2 | arachidonic acid | Δ | Δ | ○ | 52.5 |
| | 5-3 | eicosapentaenic acid | X | X | ○ | 48.8 |
| | 5-4 | docosahexaenic acid | X | X | ○ | 45.2 |
| | 5-5 | methyl docosahexaenate | X | X | ○ | 58.4 |
| | 5-6 | ethyl docosahexaenate | X | X | ◉ | 63.3 |
| Comp. Ex. (O/W) | 6-1 | γ-linolenic acid | ○ | Δ | ◉ | 52.1 |
| | 6-2 | arachidonic acid | Δ | X | ◉ | 42.3 |
| | 6-3 | eicosapentaenic acid | Δ | X | ○ | 40.6 |
| | 6-4 | docosahexaenic acid | X | X | ○ | 32.7 |
| | 6-5 | methyl docosahexaenate | X | X | ○ | 68.4 |
| | 6-6 | ethyl docosahexaenate | Δ | X | ○ | 65.7 |

As can be seen from Table 28, the O/W/O type emulsions (Examples 8-1 to 8-6) in which an organophilic clay mineral had been added in the outer oil phase were excellent in emulsification stability without separation of oil or the like, discoloring, and change in odor and exhibited a remarkably high agent remaining ratio.

In the W/O type emulsions of Comparative Examples 5-1 to 5-6, on the other hand, while stable emulsification conditions were obtained without noticeable separation of the oil phase or the like, since the agent (unsaturated fatty acid) was added in the outer oil phase, the remaining ratio of the agent was remarkably decreased due to the oxidative decomposition.

Also, in the O/W type emulsions of Comparative Examples 6-1 to 6-6, while stable emulsification conditions were obtained, agent stability was low and the degree of discoloring and change in odor was remarkable also.

EXAMPLE 9

Next, the emulsion in which a silicone type oil was added in the oil phase has been studied. Here, each of the preparation methods in Table 29 to 32 was similar to Table 3 to 6 above, respectively.

TABLE 29

O/W Type Emulsion

| Constituent | Example 9-1 |
|---|---|
| (a) Surfactant phase | |
| 1,3-Butanediol | 21 |
| Purified water | 2 |
| POE(60) hardened castor oil | 2 |
| (b) Oil phase | |
| Liquid paraffin | 32 |
| (c) Water phase | |
| Purified water | 42 |
| Emulsification stability (observation of the state) | |
| RT | ○ |
| 50° C. | ○ |
| Feel of use | X |

TABLE 30

W/O Type Emulsion

| Constituent | Example | | | | | |
|---|---|---|---|---|---|---|
| | 9-2 | 9-3 | 9-4 | 9-5 | 9-6 | 9-7 |
| (a) Surfactant | | | | | | |
| POE methylpolysiloxane copolymer*1 | 1 | 5 | 10 | — | — | — |
| POE methylpolysiloxane copolymer*2 | — | — | — | 1 | 5 | 10 |
| (b) Oil phase | | | | | | |
| Decamethylcyclopentasiloxane | 38 | 34 | 38 | 34 | 29 | 34 |
| Octamethylcyclotetrasiloxane | 1 | 1 | 1 | 1 | 1 | 1 |
| (c) Water phase | | | | | | |
| Ion-exchanged water | 60 | 60 | 60 | 60 | 60 | 60 |
| Emulsification stability (observation of the state) | | | | | | |
| RT | ○ | ○ | ○ | ○ | ○ | ○ |
| 50° C. | ○ | ○ | ○ | ○ | ○ | ○ |
| Feel of use | ○ | ○ | ○ | ○ | ○ | ○ |

TABLE 31

O/W/O Type Emulsion

| Constituent | Example | | | | | |
|---|---|---|---|---|---|---|
| | 9-8 | 9-9 | 9-10 | 9-11 | 9-12 | 9-13 |
| (a) O/W phase | | | | | | |
| O/W type emulsion of Example 9-1 | 70 | 70 | 70 | 70 | 70 | 70 |

TABLE 31-continued

O/W/O Type Emulsion

| Constituent | Example | | | | | |
|---|---|---|---|---|---|---|
| | 9-8 | 9-9 | 9-10 | 9-11 | 9-12 | 9-13 |
| (b) Outer oil phase | | | | | | |
| Decamethylcyclopentasiloxane | 29 | 25 | 20 | — | — | — |
| Octamethylcyclotetrasiloxane | — | — | — | 29 | 25 | 20 |
| (c) Lipophilic surfactant | | | | | | |
| POE methylpolysiloxane copolymer*1 | 1 | 5 | 10 | — | — | — |
| POE methylpolysiloxane copolymer*2 | — | — | — | 1 | 5 | 10 |
| Emulsification stability Observation of the state | | | | | | |
| RT | X | X | X | X | X | X |
| 50° C. | X | X | X | X | X | X |
| Inner oil phase remaining ratio (after 8 weeks at 50° C.) | <5 | <5 | <5 | <5 | <5 | <5 |
| Feel of use | Δ | Δ | Δ | Δ | Δ | Δ |

*1 and *2 are the same as those in Table 30.

TABLE 32

O/W/O type multiple emulsion

| Constituent | Example | | | | |
|---|---|---|---|---|---|
| | 9-14 | 9-15 | 9-16 | 9-17 | 9-18 |
| (a) O/W phase | | | | | |
| O/W type emulsion of Example 9-1 | 70 | 70 | 70 | 70 | 70 |
| (b) Outer oil phase | | | | | |
| Decamethylcyclopentasiloxane | 28 | 28 | 28 | 28 | 28 |
| Surfactant in outer oil phase | | | | | |
| Organophilic clay mineral* | 2 | — | — | — | — |
| Unmodified clay mineral(Beegum) | — | 2 | — | — | — |
| Benzyldimethylstearyl ammonium chloride | — | — | 2 | — | — |
| POE methylpolysiloxane copolymer** | — | — | — | 2 | — |
| Benzyldimethylstearyl ammonium chloride + POE methylpolysiloxane copolymer** | — | — | — | — | 2 |
| Emulsification stability Observation of the state | | | | | |
| RT | ○ | X | X | X | X |
| 50° C. | ○ | X | X | X | X |
| Inner oil phase remaining ratio (after 8 weeks at 50° C.) | 98 | <5 | <5 | <5 | <5 |
| Feel of use | ⊙ | ○ | ○ | ○ | ○ |

*This organophilic clay mineral was prepared in a manner similar to Preparation 1 except for using POE methylpolysiloxane copolymer Silicone SC9450N, manufactured by SINETSU KAGAKU KOGYO Co., Ltd., in stead of POE(6) lauryl ether.
**The product name is Silicone SC9450N(manufactured by SINETSU KAGAKU KOGYO Co., Ltd.).

According to Tables 29 and 30, a considerably high emulsification stability can be attained in O/W type emulsions and W/O type emulsions by selecting appropriate surfactants. However, when such a stable O/W emulsion was dispersed in the outer oil phase containing a silicone type oil to form an O/W/O type emulsion, the emulsification stability of thus obtained O/W/O emulsion was greatly deteriorated, whereby the inner oil phase exuded into the outer oil phase.

Contrary to this, as can be seen from Table 32, even when the organophilic clay mineral was added in the outer oil phase of O/W/O multiple emulsion containing a silicone type oil, an emulsification stability was quite good in both observation of the emulsification state and inner oil phase remaining ratio to be excellent.

Also, in the multiple emulsion of Example 9-14, which contained a silicone type oil and an organophilic clay mineral, when it applied on skin, good spreadability and lack of greasiness were exhibited so that the feel of use was quite excellent as compared with those of both of W/O type emulsion using a silicone type oil in Table 30 and the multiple emulsion in Table 31.

Here, when octamethylcyclotetrasiloxane was used in stead of decamethylcyclopentasiloxane in Table 32, the same result has been obtained.

Contrary to this, as can be seen from Table 32, even when the organophilic clay mineral was added in the outer oil phase of O/W/O containing a silicone type oil, an emulsion which was quite good in both of stability of the emulsification state and inner oil phase remaining ratio was obtained, and further the agent stability of retinol added in the inner oil phase was remarkably improved.

Accordingly, when the stable O/W type emulsion is simply substituted for a water phase of the stable W/O type emulsion, a stable multiple emulsion containing a silicone type oil can not be obtained. Therefor, even if each of silicone type oils and non-silicone type oils is added in separate oil phases at the time of preparation, these can not be keep stable.

On the other hand, when an organophilic clay mineral is added in the outer oil phase, as coalescence between the inner oil phase and the outer oil phase are suppressed, a stable multiple emulsion containing a silicone type oil can be obtained. And then, when each of silicone type oils and non-silicone type oils is added in separate oil phases at the time of preparation, these can be keep stable independently. Also, the feel of use is very excellent as compared with a W/O type emulsion containing a silicone type oil.

EXAMPLE 10

As explained in the following, in such a multiple emulsion, effects for preventing crystals from depositing were inspected, while 4-tert-butyl-4'-methoxydibenzoylmethane, which is a kind of ultraviolet absorber, was used as an oil-soluble agent which was hard to dissolve in a silicone type oil. Also, its feel of use was studied. Here, the methods of preparing the emulsions in the following Tables 33 to 36 were based on those in the above-mentioned Tables 3 to 6, respectively.

TABLE 33

O/W Type Emulsion

| Constituent | Example 10-1 |
|---|---|
| (a) Surfactant phase | |
| 1,3-Butanediol | 21 |
| Purified water | 2 |
| POE(60) hardened castor oil | 2 |
| (b) Oil phase | |
| Dioctyl succinate | 31 |
| 4-tert-butyl-4'-methoxydibenzoylmethane | 2 |

TABLE 33-continued

O/W Type Emulsion

| Constituent | Example 10-1 |
|---|---|
| (c) Water phase | |
| Purified water | 42 |
| Emulsification stability (observation of the state) | |
| RT | ○ |
| 50° C. | ○ |
| Crystal deposit | ○ (none) |
| Feel of use | X |

TABLE 34

W/O Type Emulsion

| | Example | |
|---|---|---|
| Constituent | 10-2 | 10-3 |
| (a) Surfactant | | |
| POE methylpolysiloxane copolymer | 5 | 5 |
| (b) Oil phase | | |
| Decamethylcyclopentasiloxane | 33 | — |
| Octamethylcyclotetrasiloxane | — | 33 |
| 4-tert-butyl-4'-methoxydibenzoylmethane | 2 | 2 |
| (c) Water phase | | |
| Ion-exchanged water | 60 | 60 |
| Emulsification stability (observation of the state) | | |
| RT | ○ | ○ |
| 50° C. | ○ | ○ |
| Crystal deposit | X (deposit) | X (deposit) |
| Feel of use | ○ | ○ |

*The product name is Silicone SC9450N(manufactured by SINETSU KAGAKU KOGYO Co., Ltd.).

TABLE 35

O/W/O Type Emulsion

| | Example | |
|---|---|---|
| Constituent | 10-4 | 10-5 |
| (a) O/W phase containing 4-tert-butyl-4'-methoxydibenzoylmethane in oil phase) | | |
| O/W type emulsion of Example 10-1 | 70 | 70 |
| (b) Outer oil phase | | |
| Decamethylcyclopentasiloxane | 25 | — |
| Octamethylcyclotetrasiloxane | — | 25 |
| (c) Lipophilic surfactant | | |
| POE methylpolysiloxane copolymer* | 5 | 5 |
| Emulsification stability Observation of the state | | |
| RT | X | X |
| 50° C. | X | X |
| Inner oil phase remaining ratio (after 8 weeks at 50° C.) | <5 | <5 |

TABLE 35-continued

O/W/O Type Emulsion

| | Example | |
|---|---|---|
| Constituent | 10-4 | 10-5 |
| Crystal deposit | X (deposit) | X (deposit) |
| Feel of use | Δ | Δ |

*The product name is Silicone SC9450N (Manufactured by SINETSU KAGAKU KOGYO Co., Ltd.).

TABLE 36

O/W/O type multiple emulsion

| | Example | |
|---|---|---|
| Constituent | 10-6 | 10-7 |
| (a) O/W phase(containing 4-tert-butyl-4'-methoxydibenzoylmethane in oil phase) | | |
| O/W type emulsion of Example 10-1 | 70 | 70 |
| (b) Outer oil phase | | |
| Decamethylcyclopentasiloxane | 28 | — |
| Octamethylcyclotetrasiloxane | — | 28 |
| (c) Lipophilic surfactant | | |
| Organophilic clay mineral* | 2 | 2 |
| Emulsification stability | | |
| Observation of the state | | |
| RT | ◯ | ◯ |
| 50° C. | ◯ | ◯ |
| Inner oil phase remaining ratio (after 8 weeks at 50° C.) | 98 | 98 |
| Crystal deposit | ◯(none) | ◯(none) |
| Feel of use | Δ | Δ |

*This was the same as that used in Table 32.

As can be seen from the above-mentioned Tables 33 and 34, O/W type and W/O type emulsions with a high emulsion stability can also be obtained when an oil-soluble agent (4-tert-butyl-4'-methoxydibenzoylmethane) is added in the oil phase. Nevertheless, when a silicone type oil is not added, their feel of use becomes inferior though no deposition of agent is seen; whereas, when the silicone type oil is added, deposition of the agent is seen over time though the feel of use improves.

Also, when the stable O/W type emulsion of Table 33 was dispersed in an oil phase containing a silicone type oil to prepare an O/W/O type emulsion in expectation of attaining the feel of use of the silicone type oil content and the effects for preventing crystals of the agent from depositing, its emulsion stability decreased so much that the inner oil phase exuded into the outer oil phase. As a result, the expected effects for preventing crystals of the agent from depositing could not be obtained. Also, the feel of use tended to deteriorate.

By contrast, when an organophilic clay mineral was added in the outer oil phase as shown in the above-mentioned Table 36, the emulsion stability was quite favorable in terms of both emulsion state and inner oil phase remaining ratio. Also, in this multiple emulsion, since coalescence of the inner phase and outer oil phase was suppressed, the slightly soluble agent(4-tert-butyl-4'-methoxydibenzoylmethane) added in the inner oil phase hardly came into contact with the silicone type oil in the outer oil phase and did not migrate to the outer oil phase, thereby effectively preventing crystals of the ultraviolet absorber from depositing. Also, its feel of use was free of greasiness and quite favorable.

As explained in the foregoing, in the multiple emulsion of the present invention, as an organophilic clay mineral is provided in the outer oil phase, coalescence of the inner oil phase and outer oil phase is suppressed even when a silicone type oil is added therein, whereby a high emulsion stability can be obtained. Accordingly, the inner oil phase and the outer oil phase can stably coexist in a single phase independently from each other. Therefore, for example, when a material which is hard to dissolve in a silicone type oil and a non-silicone type oil are added in one oil phase whereas the silicone type oil is added in the other oil phase, there can be obtained an emulsion which can prevent the material from depositing, while these ingredients stably coexist in a single system, and whose feel of use is quite excellent.

EXAMPLE 11

A preferable composition in a multiple emulsion containing a slightly-soluble agent to a silicone type oil and a silicone type oil was studied as follows:
(1) Composition

TABLE 37

Composition of O/W Type Emulsion

| Constituent | Content |
|---|---|
| (a) Surfactant phase | |
| 1,3-Butanediol | 21 |
| Purified water | 2 |
| POE(60) hardened castor oil | 2 |
| (b) Inner oil phase | |
| Dioctyl succinate | 31 |
| 4-tert-butyl-4'-methoxydibenzoylmethane | 2 |
| (c) Water phase | |
| Purified water | 42 |

TABLE 38

Composition of Outer oil phase

| Constituent | Content |
|---|---|
| (d) Surfactant | |
| Organophilic clay mineral(Preparation 1) | 7 |
| (e) Outer phase oil | |
| Decamethylcyclopentasiloxane | 93 |

TABLE 39

Constitutional Ratio of O/W/O Type Multiple Emulsion

| Example | Amount of O/W type emulsion (parts by weight) | Outer oil phase (parts by weight) |
|---|---|---|
| Example 11-1 | 50 | 50 |
| Example 11-2 | 60 | 40 |
| Example 11-3 | 70 | 30 |
| Example 11-4 | 80 | 20 |
| Example 11-5 | 35 | 65 |
| Example 11-6 | 97 | 3 |

(2) Method of preparation
The preparation method was similar to Example 2 above. Namely, first, into the mixture of uniformly dissolved ingredient (a) shown in Table 37, ingredient (b) was mixed and emulsified while being stirred. Then, ingredient (c) was added thereto and mixed therewith to yield an O/W type emulsion.

Thereafter, the outer oil phase components shown in Table 38 were mixed. In this outer oil phase, the O/W type emulsion prepared above was mixed and emulsified while being stirred to yield the aimed O/W/O type multiple emulsion. Here, the ratio of the O/W type emulsion to the outer oil phase was changed as shown in Table 39 to form Examples 11-1 to 11-6.

(3) Result

TABLE 40

Evaluation of Emulsion Characteristics

| Outer oil phase | Emulsion form directly after preparation | Emulsification stability RT | Emulsification stability 50° C. | Inner oil phase remaining ratio* | Crystal deposit |
|---|---|---|---|---|---|
| Ex. 11-1 | O/W/O | ○ | ○ | 92% | ○(none) |
| Ex. 11-2 | O/W/O | ⊚ | ○ | 93 | ○(none) |
| Ex. 11-3 | O/W/O | ⊚ | ⊚ | 98 | ○(none) |
| Ex. 11-4 | O/W/O | ⊚ | ○ | 93 | ○(none) |
| Ex. 11-5 | O/W/O | X | X | — | X(deposit) |
| Ex. 11-6 | O/W/O + O/W | X | X | — | X(deposit) |

*Inner oil remaining ratio was measured after the storage at 50° C. for one month.

As could be seen from Table 40, when the ratio of O/W type emulsion to outer oil phase is outside of the range of 2:3 to 19:1, stable multiple emulsions could not be obtained and crystal deposit of the agent added in the inner oil phase(4-tert-butyl-4'-methoxydibenzoylmethane) was observed. Contrary to this, it can be understood that, when the ratio is within the range of 2:3 to 19:1, the system has a favorable emulsification stability and crystal deposit of the agent added in the inner oil phase can be prevented.

EXAMPLE 12 AND COMPARATIVE EXAMPLE 7 TO 8

Next, O/W/O type and W/O type emulsions were prepared according to prescriptions shown in Table 41 and their effects on prevention of the crystal deposit was studied while the oil-soluble agent added in their inner oil phase was changed.

(1) Composition

TABLE 41

| Constituent | Ex. 7 (O/W/O) | Comp. Ex. 7 (W/O) | Comp. Ex. 8 (W/O) |
|---|---|---|---|
| (a) Surfactant phase | | | |
| 1,3-Butyleneglycol | 5 | 5 | 5 |
| POE(60) hardened castor oil | 1 | — | — |
| Methyl paraben | 0.1 | 0.1 | 0.1 |
| (b) Inner oil phase | | | |
| Squalane | 5 | — | — |
| Pentaerythritol tetra-2-ethylhexanoate | 5 | — | — |
| Ultraviolet absorber(cf. Table 42) | 2 | — | — |
| (c) Water phase | | | |
| Purified water | 48.9 | 59.9 | 59.9 |
| (d) Outer oil phase | | | |
| Dioctyl succinate | 9 | 9 | 30 |
| Dimethylpolysiloxane | 10 | 10 | — |
| Decamethylcyclopentasiloxane | 10 | 10 | — |
| Silicone gum | 1 | 1 | — |
| Organophilic clay mineral (Preparation 1) | 1 | 1 | 1 |
| POE(6) stearyl ether | 1 | 1 | 1 |
| POE methylpolysiloxane copolymer* | 1 | 1 | 1 |
| Ultraviolet absorber(cf. Table 42) | — | 2 | 2 |

*The product name is Silicone SC9450N(manufactured by SINETSU KAGAKU KOGYO Co., Ltd.).

(2) Method of preparation

EXAMPLE 12

It was prepared in a manner similar to Example 6.

COMPARATIVE EXAMPLE 7 AND 8

It was prepared in a manner similar to Comparative Example 2.

(3) Method of evaluation

With respect to the emulsions shown in Table 41, observation of the emulsified state was performed by the above-mentioned method, whereby changes in emulsification conditions such as change in particle size, separation, and discoloring were inspected so as to evaluate the emulsification stability. Here, the storage period was six months at 25° C. or two months at 50° C. Also, effect of prevention of the crystal deposit and the feel of use were evaluated by the above-mentioned method.

(4) Result

TABLE 42

Emulsification Stability

| | Ultraviolet absorber | Emulsification stability | Crystal deposit | Feel of use |
|---|---|---|---|---|
| Example (O/W/O) | | | | |
| 12-1 | 2,4-dihydroxybenzophenone | ⊚ | ○(none) | ⊚ |
| 12-2 | 2,2'-dihydroxy-4-methoxy benzophenone | ⊚ | ○(none) | ⊚ |
| 12-3 | 2,2'-dihydroxy-4,4-dimethoxy benzophenone | ⊚ | ○(none) | ⊚ |
| 12-4 | 2,2',4,4'-tetrahydroxybenzophenone | ⊚ | ○(none) | ⊚ |
| 12-5 | 2-hydroxy-4-methoxy benzophenone | ⊚ | ○(none) | ⊚ |
| 12-6 | 2-hydroxy-4-methoxy-4'-methyl benzophenone | ⊚ | ○(none) | ⊚ |
| 12-7 | 3-(4-methylbenzylidene)-d,1-camphor | ⊚ | ○(none) | ⊚ |
| 12-8 | 3-benzylidene-d,1-campohor | ⊚ | ○(none) | ⊚ |
| 12-9 | 4-methoxy-4'-t-butyl dibenzoylmethane | ⊚ | ○(none) | ⊚ |
| Comparative Example (W/O, containing a silicone type oil) | | | | |
| 7-1 | 2,4-dihydroxybenzophenone | X | X(deposit) | ○ |
| 7-2 | 2,2'-dihydroxy-4-methoxy benzophenone | X | X(deposit) | ○ |
| 7-3 | 2,2'-dihydroxy-4,4-dimethoxy benzophenone | X | X(deposit) | ○ |
| 7-4 | 2,2',4,4'-tetrahydroxybenzophenone | X | X(deposit) | ○ |
| 7-5 | 2-hydroxy-4-methoxy benzophenone | X | X(deposit) | ○ |
| 7-6 | 2-hydroxy-4-methoxy-4'-methyl benzophenone | X | X(deposit) | ○ |
| 7-7 | 3-(4-methylbenzylidene)-d,1-camphor | X | X(deposit) | ○ |
| 7-8 | 3-benzylidene-d,1-campohor | X | X(deposit) | ○ |
| 7-9 | 4-methoxy-4'-t-butyl dibenzoylmethane | X | X(deposit) | ○ |
| Comparative Example (W/O, containing no silicone type oils) | | | | |
| 8-1 | 2,4-dihydroxybenzophenone | X | ○(none) | X |
| 8-2 | 2,2'-dihydroxy-4-methoxy benzophenone | X | ○(none) | X |
| 8-3 | 2,2'-dihydroxy-4,4-dimethoxy benzophenone | X | ○(none) | X |
| 8-4 | 2,2',4,4'-tetrahydroxybenzophenone | X | ○(none) | X |
| 8-5 | 2-hydroxy-4-methoxy benzophenone | X | ○(none) | X |
| 8-6 | 2-hydroxy-4-methoxy-4'-methyl benzophenone | X | ○(none) | X |
| 8-7 | 3-(4-methylbenzylidene)-d,1-camphor | X | ○(none) | X |
| 8-8 | 3-benzylidene-d,1-campohor | X | ○(none) | X |
| 8-9 | 4-methoxy-4'-t-butyl dibenzoylmethane | X | ○(none) | X |

As can be seen from Table 42, though the W/O type emulsion of Comparative Example 7, in which a silicone type oil had been added in the outer oil phase together with an ultraviolet absorber, was relatively favorable in terms of lack of greasiness; deposition of the ultraviolet absorber was observed therein during storage since the ultraviolet absorber was added in the same oil phase as the silicone type oil in which the absorber had a low solubility.

On the other hand, in the case of the W/O type emulsion such as Comparative Example 8 in which a polar oil content, to which the ultraviolet absorber was highly soluble, had been added in the outer oil phase in place of silicone type oil, there was greasiness though no deposition of the ultraviolet absorber was observed over time, thereby deteriorating the feel of use.

Contrary to this, in the O/W/O type multiple emulsion of the present invention (Example 12-1 to 12-9), the crystal did not deposited and the emulsification stability was also good. Further, its feel of use has refreshness and lack of greasiness so that a cream having a good feel of use as compared with that of the emulsion of Comparative Example 5 could be obtained.

As explained in the foregoing, in the multiple emulsion of the present invention, while the components which were hard to dissolve each other, such as the agent having slight-solubility to silicone type oils, non-silicone type oils, and silicone type oils, coexist in one emulsion system, the crystal of the agent can be prevented from depositing and a multiple emulsion having very good stability of emulsification and feel of use can be obtained. Therefor, it is possible to prepare a suncare cosmetics or the like having very good feel of use and stability.

EXAMPLE 13

In O/W/O type multiple emulsions containing a silicone type oil, using an oil-soluble vitamin(vitamin A palmitate)

and an oil-soluble ultraviolet absorber(octyl dimethyl PABA), which are easily oxidized, as an oil-soluble agent, O/W/O type multiple emulsions were prepared in a manner similar to the preparation method of the above-mentioned Example 6, while the amounts of the respective ingredients were changed according to the prescriptions shown in Tables 43 and 44. As a result, it was evidenced that, as in the case of Table 20, the system has favorable emulsification stability and agent stability to oxidation even when the ratio of O/W type emulsion to outer oil phase is within the range of 2:3 to 19:1 by weight ratio.

TABLE 43

Study of Composition Ratio

| Constituent | Example | | | | |
|---|---|---|---|---|---|
| | 13-1 | 13-2 | 13-3 | 13-4 | 13-5 |
| (a) Surfactant | | | | | |
| 1,3-Butyleneglycol | 5 | 5 | 5 | 5 | 5 |
| Glycerine | 2 | 2 | 2 | 2 | 2 |
| POE(60) hardened castor oil | 1 | 1 | 1 | 1 | 1 |
| Methyl paraben | 0.1 | 0.1 | 0.1 | 0.1 | 0.1 |
| (b) Inner oil phase | | | | | |
| Squalane | 5 | 5 | 5 | 5 | 5 |
| Vitamin A palmitate | 0.2 | 0.2 | 0.2 | 0.2 | 0.2 |
| (c) Water phase | | | | | |
| Purified water | 82.2 | 76.7 | 56.7 | 36.7 | 16.7 |
| (d) Outer oil phase | | | | | |
| Octamethylcyclotetrasiloxane | 2.1 | 7.6 | 27.6 | 47.6 | 67.6 |
| Cationic denatured clay mineral (Benton-38) | 2 | 2 | 2 | 2 | 2 |
| POE methylpolysiloxane copolymer* | 0.4 | 0.4 | 0.4 | 0.4 | 0.4 |
| O/W emulsion:outer oil phase (weight ratio) | 21:1 | 9:1 | 7:3 | 5:5 | 3:7 |
| Emulsification stability (observation of the state) | | | | | |
| 50° C. | X | ◯ | ◎ | ◯ | X |
| Remaining ratio of vitamin A palmitate | X | ◎ | ◎ | ◎ | X |

*The product name is Silicone SC9450N(manufactured by SINETSU KAGAKU KOGYO Co., Ltd.).

TABLE 44

Study of Composition Ratio

| Constituent | Example | | | | |
|---|---|---|---|---|---|
| | 13-6 | 13-7 | 13-8 | 13-9 | 13-10 |
| (a) Surfactant | | | | | |
| 1,3-Butyleneglycol | 5 | 5 | 5 | 5 | 5 |
| Glycerine | 2 | 2 | 2 | 2 | 2 |
| POE(60) hardened castor oil | 1 | 1 | 1 | 1 | 1 |
| Methyl paraben | 0.1 | 0.1 | 0.1 | 0.1 | 0.1 |
| (b) Inner oil phase | | | | | |
| Octyl methoxycinnamate | 5 | 5 | 5 | 5 | 5 |
| Glyceryl tri-2-ethylhexanoate | 10 | 10 | 10 | 10 | 10 |
| Octyl dimethyl PABA** | 1 | 1 | 1 | 1 | 1 |
| (c) Water phase | | | | | |
| Purified water | 70.75 | 65.3 | 45.3 | 25.3 | 5.3 |
| (d) Outer oil phase | | | | | |
| Liquid paraffin | 0.65 | 2.6 | 9.2 | 16.0 | 22.6 |
| Decamethylcyclopentasiloxane | 1.5 | 5.0 | 18.4 | 31.6 | 45.0 |
| Cationic denatured clay mineral | 1 | 1 | 1 | 1 | 1 |

TABLE 44-continued

Study of Composition Ratio

| Constituent | Example | | | | |
|---|---|---|---|---|---|
| | 13-6 | 13-7 | 13-8 | 13-9 | 13-10 |
| (Benton-38) | | | | | |
| POE(10) sorbitan fatty acid ester | 1 | 1 | 1 | 1 | 1 |
| POE methylpolysiloxane copolymer* | 1 | 1 | 1 | 1 | 1 |
| O/W emulsion:outer oil phase (weight ratio) | 21:1 | 5:1 | 2:1 | 1:1 | 0.5:1 |
| Emulsification stability (observation of the state) | | | | | |
| 50° C. | X | ◯ | ◎ | ◯ | X |
| Remaining ratio of Octyl dimethyl PABA | X | ◎ | ◎ | ◎ | X |

*The product name is Silicone SC9450N(manufactured by SINETSU KAGAKU KOGYO CO., Ltd.).
**Octyl dimethyl PABA; Octyl p-dimethylaminobenzoate.

EXAMPLE 14 AND COMPARATIVE EXAMPLE 9 TO 10

Further, in O/W/O type multiple emulsions containing a silicone type oil, agent remaining ratio was studied when various oil-soluble vitamins were added in the inner oil phase as a agent which were easily oxidized.

(1) Composition

TABLE 45

| Constituent | Ex. 14 (O/W/O) | Comp. Ex. 9 (W/O) | Comp. Ex. 10 (O/W/O) |
|---|---|---|---|
| (a) Surfactant phase | | | |
| 1,3-Butyleneglycol | 5 | 5 | 5 |
| POE(60) hardened castor oil | 1 | — | — |
| Bentonite | — | — | 0.5 |
| Methyl paraben | 0.1 | 0.1 | 0.1 |
| (b) Inner oil phase | | | |
| Squalane | 5 | — | 5 |
| Pentaerythritol tetra-2-ethylhexanoate | 5 | — | 5 |
| Cetanol | — | — | 3 |
| POE(20) sorbitan tristearate | — | — | 1 |
| Diglycerine monooleate | — | — | 2 |
| Oil-soluble vitamin(cf. Table 46) | 1 | — | 1 |
| (c) Water phase | | | |
| Purified water | 51.9 | 52.9 | 37.4 |
| (d) Outer oil phase | | | |
| Liquid paraffin | 10 | 10 | 10 |
| Dimethylpolysiloxane | 10 | 10 | 10 |
| Decamethylcyclopentasiloxane | 10 | 10 | 10 |
| Organophilic clay mineral (Preparation 1) | 1 | 1 | 1 |
| Squalene | — | 5 | — |
| Pentaerythritol tetra-2-ethylhexanoate | — | 5 | — |
| Dextrin palmitate | — | — | 1 |
| Cetanol | — | — | 3 |
| Beeswax | — | — | 2 |
| Sorbitan sesquioleate | — | — | 3 |
| Sorbitan monostearate | — | — | 1 |
| Oil-soluble vitamin(cf. Table 46) | — | 1 | — |

(2) Method of Preparation

EXAMPLE 6

It was prepared in a manner similar to Example 6.

COMPARATIVE EXAMPLE 2

It was prepared in a manner similar to Comparative Example 2.

COMPARATIVE EXAMPLE 3

It was prepared in a manner similar to Comparative Example 3.

(3) Method of Evaluation

The emulsification stability and agent remaining ratio of thus prepared emulsion were evaluated in the above-mentioned manner. Also, discoloring and change in odor of the emulsion after being kept at 50° C. in an incubator for one month were judged in a manner similar to Example 6.

(4) Result

TABLE 46

Evaluation of Emulsion Characteristics

| Example | | Oil-soluble vitamin | Emulsification stability | | | Remaining ratio of Vitamin(%) |
|---|---|---|---|---|---|---|
| | | | Discoloring | Odor | State | |
| Example (O/W/O) | 14-1 | retinol | ⊚ | ⊚ | ○ | 90.1 |
| | 14-2 | vitamin A palmitate | ⊚ | ⊚ | ○ | 97.5 |
| | 14-3 | vitamin A acetate | ⊚ | ⊚ | ○ | 95.1 |
| | 14-4 | α-tocopherol | ⊚ | ⊚ | ○ | 92.2 |
| | 14-5 | vitamin E acetate | ⊚ | ⊚ | ○ | 99.8 |
| | 14-6 | vitamin $D_2$ | ⊚ | ⊚ | ○ | 93.2 |
| | 14-7 | β-carotene | ⊚ | ⊚ | ○ | 99.1 |
| Comp. Ex. (W/O) | 9-1 | retinol | X | X | ○ | 48.9 |
| | 9-2 | vitamin A palmitate | Δ | Δ | ○ | 67.5 |
| | 9-3 | vitamin Acetate | Δ | Δ | ○ | 50.8 |
| | 9-4 | α-tocopherol | Δ | ○ | ○ | 63.2 |
| | 9-5 | vitamin E acetate | ○ | ○ | ○ | 70.4 |
| | 9-6 | vitamin $D_2$ | Δ | ○ | ○ | 83.3 |
| | 9-7 | β-carotene | Δ | ○ | ○ | 87.1 |
| Comp. Ex. (O/W/O) | 10-1 | retinol | X | X | X | 12.2 |
| | 10-2 | vitamin A palmitate | X | X | X | 22.3 |
| | 10-3 | vitamin A acetate | X | X | X | 30.6 |
| | 10-4 | α-tocopherol | Δ | Δ | X | 63.7 |
| | 10-5 | vitamin E acetate | Δ | Δ | X | 72.4 |
| | 10-6 | vitamin $D_2$ | Δ | Δ | X | 77.7 |
| | 10-7 | β-carotene | Δ | ○ | Δ | 69.6 |

As can be seen from Table 46, the O/W/O type emulsions (Examples 14-1 to 14-7) were excellent in emulsification stability without separation of oil or the like, discoloring, and change in odor and exhibited a remarkably high agent remaining ratio.

EXAMPLE 15

Next, the multiple emulsion of the present invention in which a hydrophilic polymer was added has been studied.

TABLE 47

O/W Type Emulsion

| Constituent | Example 15-1 |
|---|---|
| (a) Surfactant phase | |
| 1,3-Butanediol | 21 |
| Purified water | 2 |
| POE(60) hardened castor oil | 2 |

TABLE 47-continued

O/W Type Emulsion

| Constituent | Example 15-1 |
|---|---|
| (b) Oil phase | |
| Liquid paraffin | 33 |
| (c) Water phase | |
| Purified water | 39 |
| Sodium alginate | 3 |

TABLE 47-continued

O/W Type Emulsion

| Constituent | Example 15-1 |
|---|---|
| Emulsification stability (observation of the state) | |
| RT | ○ |
| 50° C. | ○ |

<Method of Preparation>

In a manner similar to the method of Table 3 of Example 1 shown above, the O/W type emulsion was prepared. 1 g of 10% aqueous calcium chloride solution was added with respect to 100 g of thus obtained emulsion, thereby making sodium alginate gel.

TABLE 48

W/O Type Emulsion

| Constituent | Example 15-2 | 15-3 | 15-4 | 15-5 | 15-6 | 15-7 |
|---|---|---|---|---|---|---|
| (a) Surfactant | | | | | | |
| POE(3) oleyl ether | 1 | — | — | — | — | — |
| POE(2) oleyl ether | — | 5 | — | — | — | — |
| Sorbitan monostearate | — | — | 1 | — | — | — |
| Sorbitan monostearate | — | — | — | 5 | — | — |
| POE(10) hardened castor oil | — | — | — | — | 10 | — |
| POE(10) hardened castor oil | — | — | — | — | — | 5 |
| (b) Oil phase | | | | | | |
| Liquid paraffin | 39 | 35 | 39 | 35 | 30 | 35 |
| (c) Water phase | | | | | | |
| Ion-exchanged water | 57 | 57 | 57 | 57 | 57 | 57 |
| Sodium alginate | 3 | 3 | 3 | 3 | 3 | 3 |
| Emulsification stability (observation of the state) | | | | | | |
| RT | ○ | ○ | ○ | ○ | ○ | ○ |
| 50° C. | ○ | ○ | ○ | ○ | ○ | ○ |

<Method of Preparation>

In a manner similar to the method of Table 4 of Example 1 shown above, the W/O type emulsion was prepared. 1 g of 10% aqueous calcium chloride solution was added with respect to 100 g of thus obtained emulsion, thereby making sodium alginate gel.

TABLE 49

O/W/O Type Emulsion

| Constituent | Example 15-8 | 15-9 | 15-10 | 15-11 | 15-12 | 15-13 |
|---|---|---|---|---|---|---|
| (a) O/W phase (containing sodium alginate in the water phase) | | | | | | |
| O/W type emulsion of Example 15-1 | 70 | 70 | 70 | 70 | 70 | 70 |
| (b) Outer oil phase | | | | | | |
| Liquid paraffin | 29 | 25 | 29 | 25 | 20 | 25 |
| (c) Lipophilic surfactant | | | | | | |
| POE(3) oleyl ether | 1 | — | — | — | — | — |
| POE(2) oleyl ether | — | 5 | — | — | — | — |
| Sorbitan monostearate | — | — | 1 | — | — | — |
| Sorbitan monostearate | — | — | — | 5 | — | — |
| POE(10) hardened castor oil | — | — | — | — | 10 | — |
| POE(10) hardened castor oil | — | — | — | — | — | 5 |
| Emulsification stability Observation of the state | | | | | | |
| RT | X | X | X | X | X | X |
| 50° C. | X | X | X | X | X | X |
| Inner oil phase remaining ratio (after 8 weeks at 50° C.) | <5 | <5 | <5 | <5 | <5 | <5 |

<Method of Preparation>

In a manner similar to the method of Table 5 of Example 1 shown above, the O/W type emulsion was prepared. 1 g of 10% aqueous calcium chloride solution was added with respect to 100 g of thus obtained emulsion, thereby making sodium alginate gel.

TABLE 50

O/W/O Type Emulsion

| Constituent | Example 15-14 | 15-15 | 15-16 | 15-17 | 15-18 |
|---|---|---|---|---|---|
| (a) O/W phase (containing sodium alginate in the water phase) | | | | | |
| O/W type emulsion of Example 15-1 | 70 | 70 | 70 | 70 | 70 |
| (b) Outer oil phase | | | | | |
| Liquid paraffin | 28 | 28 | 28 | 28 | 28 |
| (c) Surfactant in outer oil phase | | | | | |
| Organophilic clay mineral (Preparation 1) | 2 | — | — | — | — |
| Unmodified clay mineral (Beegum) | — | 2 | — | — | — |
| Benzyldimethylstearyl ammonium chloride | — | — | 2 | — | — |
| POE(6)lauryl ether | — | — | — | 2 | — |
| Benzyldimethylstearyl ammonium chloride + POE(6) lauryl ether | — | — | — | — | 2 |
| Emulsification stability Observation of the state | | | | | |
| RT | ○ | X | X | X | X |
| 50° C. | ○ | X | X | X | X |
| Inner oil phase remaining ratio (after 8 weeks at 50° C.) | 98 | <5 | <5 | <5 | <5 |

<Method of Preparation>

In a manner similar to the method of Table 6 of Example 1 shown above, the O/W type emulsion was prepared. 1 g of 10% aqueous calcium chloride solution was added with respect to 100 g of thus obtained emulsion, thereby making sodium alginate gel.

According to Tables 47 and 48, a considerably high emulsification stability can be attained in O/W type emulsions and W/O type emulsions by selecting appropriate surfactants. However, when a stable O/W emulsion was dispersed in the outer oil phase to form an O/W/O type emulsion, the emulsification stability of thus obtained O/W/O emulsion was greatly deteriorated, whereby the inner oil phase exuded into the outer oil phase.

Also, as can be seen from Table 49, even when hydrophilic polymer which is commonly effective to stabilize emulsification state is added in the water phase of O/W/O type multiple emulsion, its stability cannot be improved greatly.

Contrary to this, as shown in Table 50, even in the case where a hydrophilic polymer is added in the water phase, when an organophilic clay mineral is added in the outer oil phase, the emulsification stability is very good in terms of observation of emulsified state and inner oil phase remaining ratio, thereby yielding an excellent effect of emulsification stabilization.

Accordingly, the emulsification stability of the multiple emulsion cannot be improved when the stable O/W type emulsion is simply substituted for a water phase of the stable W/O type emulsion, even though a hydrophilic polymer is added in the water phase to be made to gel. The effect on the stability of the multiple emulsion can be obtained specifically by adding the organophilic clay mineral.

EXAMPLE 16

A preferable composition of the multiple emulsion of the present invention was studied in the case adding a hydrophilic polymer in the water phase.

47

(1) Composition

TABLE 51

Composition of O/W Type Emulsion

| Constituent | Content |
| --- | --- |
| (a) Surfactant phase | |
| 1,3-Butanediol | 21 |
| Purified water | 2 |
| POE(60) hardened castor oil | 2 |
| (b) Inner oil phase | |
| Liquid paraffin | 33 |
| (c) Water phase | |
| Purified water | 39 |
| Sodium alginate | 3 |

TABLE 52

Composition of Outer oil phase

| Constituent | Content |
| --- | --- |
| (d) Surfactant | |
| Organophilic clay mineral of Preparation 1 | 7 |
| (e) Outer phase oil | |
| Liquid paraffin | 93 |

TABLE 53

Constitutional Ratio of O/W/O Type Multiple Emulsion

| Example | Amount of O/W type emulsion (parts by weight) | Amount of outer oil phase (parts by weight) |
| --- | --- | --- |
| Example 16-1 | 50 | 50 |
| Example 16-2 | 60 | 40 |
| Example 16-3 | 70 | 30 |
| Example 16-4 | 80 | 20 |
| Example 16-5 | 35 | 65 |
| Example 16-6 | 97 | 3 |

(2) Method of preparation

First, into the mixture of uniformly dissolved ingredient (a) shown in Table 51, ingredient (b) was mixed and emulsified while being stirred. Then, ingredient (c) was added thereto and mixed therewith to yield an O/W type emulsion.

Thereafter, the outer oil phase component shown in Table 52 was mixed. In this outer oil phase, the O/W type emulsion prepared above was mixed and emulsified while being stirred to yield the aimed O/W/O type multiple emulsion and then 1 g of 10% aqueous calcium chloride solution was added with respect to 100 g of thus obtained emulsion to make sodium alginate gel, thereby yielding aimed multiple emulsion. Here, the ratio of the O/W type emulsion to the outer oil phase was changed as shown in Table 53 to form Examples 16-1 to 16-6.

48

(3) Result

TABLE 54

Evaluation of Emulsion Characteristics

| Outer oil phase | Emulsion form directly after preparation | Emulsification stability RT | Emulsification stability 50° C. | Inner oil phase remaining ratio* (50° C., 1 month) |
| --- | --- | --- | --- | --- |
| Ex. 16-1 | O/W/O | ○ | ○ | 93.0% |
| Ex. 16-2 | O/W/O | ⊚ | ○ | 95.5 |
| Ex. 16-3 | O/W/O | ⊚ | ⊚ | 98.6 |
| Ex. 16-4 | O/W/O | ⊚ | ○ | 92.8 |
| Ex. 16-5 | O/W/O | X | X | — |
| Ex. 16-6 | O/W/O + O/W | X | X | — |

As can be seen from Table 54, in the multiple emulsion of the present invention, even when a hydrophilic polymer is added in the water phase, the preferable ratio of O/W type emulsion to the outer oil phase is within the range of 2:3 to 19:1.

COMPARATIVE EXAMPLE 11

Outer oil phases were prepared according to compositions in the following Table 55 to form Comparative Examples 11-1 to 11-6. In each outer oil phase, the lipophilic surfactant commonly used for preparing the conventional W/O type emulsion was used therein.

Further, an O/W type emulsion prepared in a manner similar to Table 51 of Example 16 and each of the outer oil phases of Comparative Examples shown in Table 55 were mixed and emulsified together at a ratio of 7:3 by weight and then 1 g of 10% aqueous calcium chloride solution was added with respect to 100 g of thus obtained emulsion to make sodium alginate gel, thereby yielding aimed O/W/O type multiple emulsion.

The emulsification stability of thus prepared emulsion is shown in Table 56.

TABLE 55

Composition of Outer Oil Phase

| Outer oil phase | Lipophilic surfactant (parts by weight) | Oil (parts by weight) |
| --- | --- | --- |
| Comp. Ex. 11-1 | POE(3)oleyl ether (1) | liquid paraffin (99) |
| Comp. Ex. 11-2 | POE(3)oleyl ether (5) | liquid paraffin (95) |
| Comp. Ex. 11-3 | sorbitan monostearate (1) | liquid paraffin (99) |
| Comp. Ex. 11-4 | sorbitan monostearate (5) | liquid paraffin (95) |
| Comp. Ex. 11-5 | POE(10) hardened castor oil (10) | liquid paraffin (90) |
| Comp. Ex. 11-6 | POE(10) hardened castor oil (5) | liquid paraffin (95) |

TABLE 56

Evaluation of Emulsion Characteristics

| Outer oil phase | Emulsion form directly after preparation | Emulsion stability RT | Emulsion stability 50° C. |
|---|---|---|---|
| Comp. Ex. 11-1 | O/W/O | X | X |
| Comp. Ex. 11-2 | O/W/O + O/W | X | X |
| Comp. Ex. 11-3 | O/W/O | X | X |
| Comp. Ex. 11-4 | O/W/O | X | X |
| Comp. Ex. 11-5 | O/W/O + O/W | X | X |
| Comp. Ex. 11-6 | O/W/O + O/W | X | X |

When the evaluation in Table 54 and that of in Table 56 are compared with each other, it can be seen that Examples 16-1 to 16-4 of the present invention are superior in emulsification stability to Comparative Examples 11-1 to 11-6.

EXAMPLE 17 AND COMPARATIVE EXAMPLE 12

As explained in the following, effects of the multiple emulsion containing a hydrophilic polymer added therein when applied on skin were evaluated in terms of skin irritation and continuance of the effects.

Namely, while the hydrophilic polymer added to the water phase is effective in stabilizing the composition, particular effects are seen in gradually releasing the medically active components in the inner oil phase. According to this gradual releasing, the agent can be prevented from acutely acting on the skin, while the effects of the agent can be continued.

Here, specifically, the samples having compositions of the following Table 57 were applied to the upper arms of a panel consisting of 25 each of males and females, and irritation such as stingingness was evaluated 30 minutes after the application, whereas the continuance of effects was evaluated three hours after the application. Each judgement standard was as follows;

Irritation to Skin

⊚: Among 50 panels, 0 to 5 panels felt stingingness to skin.

O: Among 50 panels, 6 to 20 panels felt stingingness to skin.

Δ: Among 50 panels, 21 to 35 panels felt stingingness to skin.

X: Among 50 panels, 36 to 50 panels felt stingingness to skin.

Continuance of Effects

⊚: Among 50 panels, 36 to 50 panels felt continuance of effects.

O: Among 50 panels, 21 to 35 panels felt continuance of effects.

Δ: Among 50 panels, 6 to 20 panels felt continuance of effects.

X: Among 50 panels, 0 to 5 panels felt continuance of effects.

TABLE 57

| Constituent | Example 17-1 | Example 17-2 | Comp. Ex. 12-1 | Comp. Ex. 12-2 | Comp. Ex. 12-3 |
|---|---|---|---|---|---|
| Emulsification Form (a) | O/W/O | O/W/O | O/W | W/O | O/W/O |
| 1,3-Butyleneglycol | 10.5 | — | 10.5 | 10.5 | — |
| Purified water | 1 | — | 1 | — | — |
| POE(60) hardened castor oil | 1 | — | 1 | — | — |
| POE(25) cetyl ether | — | 3 | — | — | — |
| Glyceryl monostearate | — | 2 | — | — | — |
| (a') | | | | | |
| Glycerine | — | 5 | — | — | 5 |
| Bentonite | — | — | — | — | 0.5 |
| (b) | | | | | |
| Liquid paraffin | 15.4 | 9 | 28.9 | 26.9 | 14.4 |
| POE(20) sorbitan tristearate | — | — | — | — | 1 |
| Glyceryl trioctanoate | — | 3 | — | — | — |
| Olive oil | — | 2 | — | — | — |
| Stearyl alchol | — | 0.5 | — | — | — |
| (c) | | | | | |
| nonylic acid vanillic acid nonylamide | 1 | 1 | 1 | 1 | 1 |
| (d) | | | | | |
| Purified water | TO 100 | | | | |
| (e) | | | | | |
| Organophilic clay mineral (Preparation 2) | 2 | 2 | — | 2 | 1 |

TABLE 57-continued

| | Example | | Comp. Ex. | | |
|---|---|---|---|---|---|
| Constituent | 17-1 | 17-2 | 12-1 | 12-2 | 12-3 |
| (e') | | | | | |
| Dextrin stearate | — | — | — | — | 1 |
| (f) | | | | | |
| Liquid paraffin | 28 | 28 | — | — | 29 |
| (g) | | | | | |
| Cardrant | 1 | 1 | — | — | — |
| (h) | | | | | |
| Kertrol | — | — | 1 | — | — |
| (i) | | | | | |
| 1N—NaOH | 0.2 | 0.2 | — | — | — |
| (j) | | | | | |
| 1N—HCl | 0.2 | 0.2 | — | — | — |
| Irritation to skin (Stingingness) | ⊚ | ○ | Δ | X | ○ |
| Continuance of effects | ⊚ | ○ | X | X | Δ |

As shown in Table 57, in the O/W/O multiple emulsion in accordance with the present invention, as compared with the other simple emulsion system, low irritation to skin and continuance of effects could be obtained. Also, the O/W/O type multiple emulsion prepared by Comparative Example 12-3 could not exhibit a enough effect in gradually releasing the drug because it did not contain a hydrophilic polymer in the water phase.

Here, the method of preparing each composition is as follows;

EXAMPLE 17-1

After ingredient (a) and ingredient (b)+(c) were separately melted to be uniform, ingredient (b)+(c) was mixed and emulsified in ingredient (a) while being stirred and then ingredient (d)+(g)+(i) was added thereto, thereby preparing an O/W type emulsion. While being stirred, thus obtained O/W type emulsion was mixed and emulsified in ingredient (e)+(f), which had been mixed beforehand, and then ingredient (j) was added thereto, thereby yielding the aimed O/W/O type multiple emulsion.

EXAMPLE 17-2

After ingredient (a)+(b)+(c) and ingredient (a')+(d) were separately melted to be uniform, by using the phase inversion method as it was called, (a')+(d) was mixed and emulsified in ingredient (a)+(b)+(c) while being stirred, thereby yielding an O/W type emulsion. Into ingredient (g) suspended in a small amount of purified water, ingredient (i) was added and dissolved therein, thereby yielding an O/W type emulsion containing cardrant. While being stirred, thus obtained O/W type emulsion containing cardrant was mixed and emulsified in ingredient (e)+(f), which had been mixed beforehand, and then ingredient (j) was added thereto, thereby yielding the aimed O/W/O type multiple emulsion.

COMPARATIVE EXAMPLE 12-1

Into ingredient (a) uniformly mixed and dissolved, ingredient (b)+(c) was mixed and emulsified therein while being stirred. Ingredients (d) and ingredient (h) were admixed thereto, thereby yielding the aimed O/W type emulsion.

EXAMPLE 12-2

After ingredient (b)+(c)+(e) was uniformly mixed and dissolved while being stirred, ingredient (a)+(d) was mixed and emulsified therein while being stirred, thereby yielding the aimed W/O type emulsion.

COMPARATIVE EXAMPLE 12-3

After ingredient (a')+(d) and ingredient (b)+(c) were separately heated and melted, ingredient (b)+(c) was mixed, dispersed, and emulsified in ingredient (a')+(d) while being stirred, thereby yielding an O/W type emulsion. Then, this O/W type emulsion was mixed in ingredient (e')+(f), which had been heated and mixed at 80° C. beforehand, and then cooled to 30° C. while being stirred, thereby yielding the aimed O/W/O type multiple emulsion.

EXAMPLE 18 AND COMPARATIVE EXAMPLE 13

Next, emulsions were prepared in a manner similar to Table 57 shown above except for using methyl salicylate in stead of nonyl vanillic acid nonylamide and their evaluation had been performed. The result was shown in Table 58 below.

TABLE 58

| | Example | | Comp. Ex. | | |
|---|---|---|---|---|---|
| Constituent | 18-1 | 18-2 | 13-1 | 13-2 | 13-3 |
| Irritation to skin (Stingingness) | ⊚ | ○ | Δ | Δ | Δ |
| Continuance of effects | ⊚ | ○ | X | X | Δ |

As shown in Table 58, in the multiple emulsion in accordance with the present invention, excellent effect of decreasing irritation to skin and continuance of effect of the drug could be obtained.

As explained in the foregoing, in the multiple emulsion and method of preparing the same in accordance with the present invention, the following advantageous effects can be obtained:

(1) Since a stable and uniform multiple emulsion can be obtained easily at normal temperature without necessitating any special emulsifier or a heating and rapid cooling step, its manufacturing cost becomes low.

(2) Since a stable and uniform multiple emulsion can be obtained easily at normal temperature without necessitating a heating and rapid cooling step, a thermally unstable ingredient can be stably compounded therein.

(3) A stable and uniform O/W/O type multiple emulsion can be obtained and, when an oil-soluble agent is added in its inner oil phase, an excellent agent stability can be obtained as well.

(4) When the water phase is made to gel by using a hydrophilic polymer, the drug dissolved in the inner oil phase can be released gradually, thereby yielding the effect on decreasing irritation and continuance of the effects of the drug.

What is claimed is:

1. An oil-in-water-in-oil multiple emulsion comprising an oil-in-water emulsion dispersed in a continuous outer oil phase, wherein said outer oil phase contains an organophilic clay mineral, whereby said organophilic clay mineral is an inclusion compound which is formed by cation exchange reaction between a water swellable-clay mineral and a quaternary ammonium cation and by physical adsorption with a nonionic surfactant.

2. A multiple emulsion as claimed in claim 1, wherein a blending ratio of the oil-in-water type emulsion to the outer oil phase is within a range of 2:3 to 19:1 by weight ratio.

3. A multiple emulsion as claimed in claim 1, wherein a silicone type oil is contained in the oil phase.

4. A multiple emulsion as claimed in claim 3, wherein the silicone type oil is contained in the outer oil phase.

5. A multiple emulsion as claimed in claim 3, wherein the silicone type oil is within a range of 5 to 60 weight % with respect to a whole amount of the multiple emulsion.

6. A multiple emulsion as claimed in claim 3, wherein the silicone type oil has a boiling point which is 200° C. or less.

7. A multiple emulsion as claimed in claim 1, wherein an inner oil phase contains an oil-soluble material.

8. A multiple emulsion as claimed in claim 7, wherein the oil-soluble material contained in the inner oil phase is slightly soluble in a silicone type oil and the silicone type oil is blended in the outer oil phase.

9. A multiple emulsion as claimed in claim 7, wherein the oil-soluble material contained in the inner oil phase is one or more agent selected from the group consisting of oil-soluble vitamins, oil-soluble ultraviolet absorbers, and unsaturated fatty acids and the derivatives thereof which are easily oxidized.

10. A multiple emulsion as claimed in claim 1, wherein a water phase contains a hydrophilic polymer.

11. A multiple emulsion as claimed in claim 10, wherein the hydrophilic polymer is one or more selected from the group of sodium alginate, carrageenan, xanthan gum, gelatin, curdlan, agar, glucomannan, starch, hyaluronic acid, scleroglucan, schizophyllan, lentinan, paramylon, callose, laminaran, cellulose, methylcellulose, ethylcellulose, nitrocellulose, gum arabic, polyvinyl alcohol, carboxyvinyl polymer, carboxymethylcellulose, hydroxyethylcellulose, polyethylene glycol, tragacanth gum, garactan, guar gum, carob gum, karaya gum, pectin, guince seed, argecolloids, glycyrrhizinic acid, dextran, puluran, collagen, casein, albumen, carboxymethyl starch, methylhydroxypropyl starch, methylhydroxypropylcellulose, sodium cellulose sulfate, hydroxypropylcellulose, propylene glycol alginate, polyvinylmethyl ether, polyvinyl pyrrolidone, polyoxyethylene copolymer, sodium polyacrylate, polyethylacrylate, polyacryl amide, and polyethlene imine.

12. The oil-in-water-in-oil type multiple emulsion according to claim 1, wherein said nonionic surfactant has an HLB value of more than 8 and less than 16.

13. A method of preparing an oil-in-water-in oil multiple emulsion which comprises the steps of:
  preparing an oil in water-soluble solvent emulsion by blending components of an inner oil phase into a mixture of a hydrophilic nonionic surfactant and a water-soluble solvent;
  preparing an oil-in-water emulsion by blending components of a water phase into said oil in water-soluble solvent emulsion; and
  preparing an oil-in-water-in-oil multiple emulsion by dispersing and emulsifying said oil-in-water emulsion in a mixture of components of an outer oil phase which contains an organophilic clay mineral, whereby said organophilic clay mineral is an inclusion compound which is formed by cation exchange reaction between a water swellable-clay mineral and a quaternary ammonium cation and by physical adsorption with a nonionic surfactant.

14. A method as claimed in claim 13, wherein a silicone type oil is contained in the oil phase.

15. A method as claimed in claim 14, wherein the silicone type oil is contained in the outer oil phase.

16. A method as claimed in claim 13, wherein the inner oil phase contains an oil-soluble material.

17. A method as claimed in claim 16, wherein the oil-soluble material included in the inner oil phase is slightly soluble in a silicone type oil and the silicone type oil is contained in the outer oil phase.

18. A method as claimed in claim 16, wherein the oil-soluble material contained in the inner oil phase is one or more agent selected from a group consisting of oil-soluble vitamins, oil-soluble ultraviolet absorbers, and unsaturated fatty acids and the derivatives thereof which are easily oxidized.

19. A method as claimed in claim 13, which comprises the steps of:
  preparing an oil in water-soluble solvent emulsion by blending components of an inner oil phase into a mixture of a hydrophilic nonionic surfactant and a water-soluble solvent;
  preparing an oil-in-water emulsion by blending components of a water phase which contains water and a hydrophilic polymer into said oil in water-soluble solvent emulsion;
  preparing an oil-in-water-in-oil multiple emulsion by dispersing and emulsifying said oil-in-water emulsion in a mixture of components of an outer oil phase which contains an organophilic clay mineral, whereby said organophilic clay mineral is an inclusion compound which is formed by cation exchange reaction between a water swellable-clay mineral and a quaternary ammonium cation and by physical adsorption with a nonionic surfactant; and making a water phase gel by blending gelling agent of the hydrophilic polymer into said oil-in-water-in-oil multiple emulsion.

* * * * *